United States Patent [19]

Parker et al.

[11] Patent Number: 5,672,350
[45] Date of Patent: Sep. 30, 1997

[54] RECOMBINANT BOVINE CORONAVIRUS E2 AND E3 POLYPEPTIDES AND VACCINES

[75] Inventors: Michael D. Parker; Graham J. Cox; Lorne A. Babiuk, all of Saskatoon, Canada

[73] Assignee: Veterinary Infectious Disease Organization, Saskatchewan, Canada

[21] Appl. No.: 171,763

[22] Filed: Dec. 22, 1993

Related U.S. Application Data

[63] Continuation of Ser. No. 811,422, Dec. 19, 1991, abandoned, which is a continuation-in-part of Ser. No. 779,500, Oct. 18, 1991, abandoned, which is a continuation-in-part of Ser. No. 397,689, Aug. 22, 1989, abandoned.

[51] Int. Cl.$^6$ .................................................. A61K 39/215
[52] U.S. Cl. ........................... 424/221.1; 424/185.1; 435/69.3; 530/350; 530/395; 536/23.72
[58] Field of Search ..................... 424/184.1, 186.1, 424/221.1, 93.6, 185.1; 514/2, 8; 530/350, 395, 806, 826; 435/69.3; 536/23.72

[56] References Cited

U.S. PATENT DOCUMENTS

| | | | |
|---|---|---|---|
| 3,873,422 | 3/1975 | Mebus | 195/1.3 |
| 3,914,408 | 10/1975 | Mebus | 424/89 |
| 3,919,412 | 11/1975 | Mebus | 424/89 |
| 3,919,413 | 11/1975 | Mebus | 424/89 |
| 4,567,042 | 1/1986 | Acree et al. | 424/89 |
| 4,567,043 | 1/1986 | Acree et al. | 424/89 |
| 4,904,468 | 2/1990 | Gill et al. | 424/89 |
| 5,013,663 | 5/1991 | Acree et al. | 435/237 |

OTHER PUBLICATIONS

Cuatrecasas, P., et al., Annual Review of Bicohemistry 40:359–378 (1971), "Affinity chromatography".
Bürki, F., et al., J. Vet. Med. 33:241–252 (1986), "Reduction of rotavirus–, coronavirus, and E. coli –associated calf–diarrheas in a large–size dairy herd by means of dam vaccination with a triple–vaccine".
Deregt, D., et al., Adv. Exp. Med. Biol. 218:473–474 (1987), "Monoclonal antibodies to two bovine coronavirus glycoproteins neutralize virus infectivity."
Deregt, D., et al., Virology 161:410–420 (1987), "Monoclonal antibodies to bovine coronavirus: characteristics and topographical mapping of neutralizing epitopes on the E2 and E3 glycoproteins."
Lapps, W., et al., Virology 157:47–57 (1987), "Sequence analysis of the bovine nucleocapsid and matrix protein genes".
Heckert, R. A., et al., Am. Vet. Res. 52(5):700–708 (1991), "Mucosal and systemic antibody responses to bovine coronavirus structural proteins in experimentally challenge–exposed calves fed low or high amounts of colostral antibodies".
Mullaney, T. P., et al., Am. J. Vet. Res. 49(2):156–159 (Feb. 1988), "Humoral immune response of the bovine fetus to in utero vaccination with attenuated bovine coronavirus".

Murakami, T., et al., Jpn J. Vet. Sci. 48(2):237–245 (1986), "Protective effect of orally administered immunoglobulins against experimental calf diarrhea".
Nagy, E., et al., Virology 176:426–438 (1990), "cloning and expression of NDV Hemagglutinin–Neuraminidase cDNA in a baculovirus expression vector system".
Parker, M. D., et al., J. Virology 64(4):1625–1629 (Apr. 1990), "Expression and secretion of the bovine coronavirus hemagglutinin–esterase glycoprotein by insect cells infected with recombinant baculovirus".
Thomsen, D.R., et al., J. Cellular Biochem. 43:67–79 (1990), "Structure of O–glycosidically linked oligosaccharides synthesized by the insect cell line Sf9".
Van Wyke, K. L., et al., Virology 160:465–472 (1987), "Expression of biologically active and antigenically authentic parainfluenza type 3 virus hemagglutinin–neurominidase glycoprotein by a recombinant baculovirus".
Wathen, M.W., et al., J. Gen. Virology 70:2625–2635 (1989), "Characterization of a novel human respiratory syncytial virus chimeric FG glycoprotein expressed using a baculovirus vector".
Yoden, S., et al., Virology 173:615–623 (1989), "Expression of the peplomer glycoprotein of murine coronavirus JHM using a baculovirus vector".
*Infectious Diseases and Medical Microbiology*, A. I. Braude (ed.), pp. 552–553 W.B. Saunders Co., Philadelphia, Pa (1986).
de Groot et al., (1987) *Adv. Exp. Med. Biol.* 218:31–38.
Cavanagh (1983) *J. gen. Virol.* 64:2577–2583.
Cavanagh et al., (1984) *Avian Pathology* 13:573–583.
Mockett et al., (1984) *J. gen. Virol.* 65:2281–2286.
Tomley et al., (1987) *J. gen. Virol.* 68:2291–2298.
Niesters et al., (1986) *Virus Res.* 5:253–263.
Laude et al., (1986) *J. gen Virol.* 67:19–130.
Sturman et al., (1985) *J. Virol.* 56:904–911.
Dalziel et al., (1986) *J. Virol.* 59:463–471.
Talbot et al., (1984) *Virology* 132:250–260.
Bachmeier et al., (1984) *Virology* 132:261–270.
Wege et al., (1984) *J. gen Virol.* 65:1931–1942.
Schmidt et al., (1987) *J. gen Virol.* 68:47–56.
Makino et al., (1987) *Proc. Natl. Acad. Sci. USA* 84:6567–6571.
Dea et al., (1980) *Am. J. Vet. Res.* 41:30–38.
King et al., (1984) *J. Virol.* 42:700–707.
Hogue et al., (1984) *J. Virol.* 51:384–388.
King et al., (1985) *Virus Res.* 2:53–59.
Lapps et al., (1987) *Virology* 157:47–57.
Deregt et al., (1987) *Virology* 161:410–420.

(List continued on next page.)

Primary Examiner—Thomas M. Cunningham
Attorney, Agent, or Firm—Morrison & Foerster LLP

[57] ABSTRACT

Nucleic acid sequences encoding the Bovine Coronavirus E2 (or BCV S) and E3 (or BCV HE) structural glycoproteins and methods of producing these proteins, including recombinant expression, e.g., in mammalian or insect cells, are provided. The E2 and E3 proteins or antigenic fragments thereof are useful components for Bovine Coronavirus vaccines and methods of treatment.

18 Claims, 36 Drawing Sheets

OTHER PUBLICATIONS

Parker et al., (1989) *J. gen. Virol.* 70:155–164.
Collins et al., (1982) *Virology* 119:358–3712.
Deregt et al., (1987) *J. gen. Virol.* 68:2863–2877.
Fleming et al., (1986) *J. Virol.* 58:869–875.
Keck et al., (1988) *Virus Res.* 9:343–356.
Yoo et al., (1991) *Virology* 183:91–98.
Fields et al., eds., *Fundamental Virology*, Raven Press, New York, p. 514.
de Groot et al., (1987) *J. gen. Virol.* 68:2639–2646.
Young et al., (1983) *Proc. Natl. Acad. Sci. USA* 80:1194–119.

```
CCATAA TCTA AAC ATG TTT TTG ATA CTT TTA ATT TCC TTA CCA ATG GCT    49
            Met Phe Leu Ile Leu Leu Ile Ser Leu Pro Met Ala
             1                    5                   10

TTT GCT GTT ATA GGA GAT TTA AAG TGT ACT ACG GTT TCC ATT AAT GAT    97
Phe Ala Val Ile Gly Asp Leu Lys Cys Thr Thr Val Ser Ile Asn Asp
             15                  20                  25

GTT GAC ACC GGT GCT CCC TCT ATT AGC ACT GAT ATT GTC GAT GTT ACT   145
Val Asp Thr Gly Ala Pro Ser Ile Ser Thr Asp Ile Val Asp Val Thr
     30                  35                  40

AAT GGT TTA GGT ACT TAT GTT TTA GAT CGT GTG TAT TTA AAT ACT       193
Asn Gly Leu Gly Thr Tyr Val Leu Asp Arg Val Tyr Leu Asn Thr
 45                  50                  55                  60

ACG TTG TTG CTT AAT GGT TAC TAC CCT ACT TCA GGT TCT ACA TAT CGT   241
Thr Leu Leu Leu Asn Gly Tyr Tyr Pro Thr Ser Gly Ser Thr Tyr Arg
 65                  70                  75
```

FIG. 3A

```
AAT ATG GCA CTG AAG GGA ACT TTA CTA TTG AGC AGA CTA TGG TTT AAA    289
Asn Met Ala Leu Lys Gly Thr Leu Leu Leu Ser Arg Leu Trp Phe Lys
         80                     85                     90

CCA CCT TTT CTT TCT GAT TTT ATT AAT GGT ATT TTT GCT AAG GTC AAA    337
Pro Pro Phe Leu Ser Asp Phe Ile Asn Gly Ile Phe Ala Lys Val Lys
             95                    100                    105

AAT ACC AAG GTT ATT AAA AAG GGT GTA ATG TAT AGT GAG TTT CCT GCT    385
Asn Thr Lys Val Ile Lys Lys Gly Val Met Tyr Ser Glu Phe Pro Ala
        110                    115                    120

ATA ACT ATA GGT AGT ACT TTT GTA AAT ACA TCC TAT AGT GTG GTA GTA    433
Ile Thr Ile Gly Ser Thr Phe Val Asn Thr Ser Tyr Ser Val Val Val
            125                    130                    135                140

CAA CCA CAT ACT ACC AAT TTG GAT AAT AAA TTA CAA GGT CTC TTA GAG    481
Gln Pro His Thr Thr Asn Leu Asp Asn Lys Leu Gln Gly Leu Leu Glu
        145                    150                    155
```

FIG. 3B

```
ATC TCT GTT TGC CAG TAT ACT ATG TGC GAG TAC CCA CAT ACG ATT TGT    529
Ile Ser Val Cys Gln Tyr Thr Met Cys Glu Tyr Pro His Thr Ile Cys
            160                 165                 170

CAT CCT AAG CTG GGT AAT AAA CGC GTA GAA CTA TGG CAT TGG GAT ACA    577
His Pro Lys Leu Gly Asn Lys Arg Val Glu Leu Trp His Trp Asp Thr
        175                 180                 185

GGT GTT GTT TCC TGT TTA TAT AAG CGT AAT TTC ACA TAT GAT GTG AAT    625
Gly Val Val Ser Cys Leu Tyr Lys Arg Asn Phe Thr Tyr Asp Val Asn
                190                 195                 200

GCT GAT TAC TTG TAT TTC CAT TTT TAT CAA GAA GGT GGT ACT TTT TAT    673
Ala Asp Tyr Leu Tyr Phe His Phe Tyr Gln Glu Gly Gly Thr Phe Tyr
205                 210                 215                 220

GCA TAT TTT ACA GAC ACT GGT GTT GTT ACT AAG TTT CTG TTT AAT GTT    721
Ala Tyr Phe Thr Asp Thr Gly Val Val Thr Lys Phe Leu Phe Asn Val
            225                 230                 235
```

FIG. 3C

```
TAT TTA GGC ACG GTG CTT TCA CAT TAT TAT GTC CTG CCT TTG ACT TGT    769
Tyr Leu Gly Thr Val Leu Ser His Tyr Tyr Val Leu Pro Leu Thr Cys
240                 245                 250

TCT AGT GCT ATG ACT TTA GAA TAT TGG GTT ACA CCT CTC ACT TCT AAA    817
Ser Ser Ala Met Thr Leu Glu Tyr Trp Val Thr Pro Leu Thr Ser Lys
        255                 260                 265

CAA TAT TTA CTA GCT TTC AAT CAA GAT GGT GTT ATT TTT AAT GCT GTT    865
Gln Tyr Leu Leu Ala Phe Asn Gln Asp Gly Val Ile Phe Asn Ala Val
270                 275                 280

GAT TGT AAG AGT GAT TTT ATG AGT GAG ATT AAG TGT AAA ACA CTA TCT    913
Asp Cys Lys Ser Asp Phe Met Ser Glu Ile Lys Cys Lys Thr Leu Ser
285                 290                 295                 300

ATA GCA CCA TCT ACT GGT GTT TAT GAA TTA AAC GGT TAC ACT GTT CAG    961
Ile Ala Pro Ser Thr Gly Val Tyr Glu Leu Asn Gly Tyr Thr Val Gln
        305                 310                 315
```

FIG. 3D

```
CCA ATT GCA GAT GTT TAC CGA CGT ATA CCT AAT CTT CCC GAT TGT AAT    1009
Pro Ile Ala Asp Val Tyr Arg Arg Ile Pro Asn Leu Pro Asp Cys Asn
        320                     325                     330

ATA GAG GCT TGG CTT AAT GAT AAG TCG GTG CCC TCT CCA TTA AAT TGG    1057
Ile Glu Ala Trp Leu Asn Asp Lys Ser Val Pro Ser Pro Leu Asn Trp
        335                     340                     345

GAA CGT AAG ACC TTT TCA AAT TGT AAT TTT AAT ATG AGC AGC CTG ATG    1105
Glu Arg Lys Thr Phe Ser Asn Cys Asn Phe Asn Met Ser Ser Leu Met
350                     355                     360

TCT TTT ATT CAG GCA GAC TCA GAC TCT TTC ACT TGT AAT AAT ATT GAT GCT GCT    1153
Ser Phe Ile Gln Ala Asp Ser Phe Thr Cys Asn Asn Ile Asp Ala Ala
365                     370                     375                 380

AAG ATA TAT GGT ATG TGT TTT TCC AGC ATA ACT ATA GAT AAG TTT GCT    1201
Lys Ile Tyr Gly Met Cys Phe Ser Ser Ile Thr Ile Asp Lys Phe Ala
            385                     390                     395
```

FIG. 3E

```
ATA CCC AAT GGT AGG AAG GTT GAC CTA CAA TTG GGC AAT TTG GGC TAT    1249
Ile Pro Asn Gly Arg Lys Val Asp Leu Gln Leu Gly Asn Leu Gly Tyr
            400                 405                 410

TTG CAG TCT TTT AAC TAT AGA ATT GAT ACT ACT GCT ACA AGT TGT CAG    1297
Leu Gln Ser Phe Asn Tyr Arg Ile Asp Thr Thr Ala Thr Ser Cys Gln
        415                 420                 425

TTG TAT TAT AAT TTA CCT GCT GCT AAT GTT TCT GTT AGC AGG TTT AAT    1345
Leu Tyr Tyr Asn Leu Pro Ala Ala Asn Val Ser Val Ser Arg Phe Asn
    430                 435                 440

CCT TCT ACT TGG AAT AGG AGA TTT GGT TTT ACA GAA CAA TTT GTT TTT    1393
Pro Ser Thr Trp Asn Arg Arg Phe Gly Phe Thr Glu Gln Phe Val Phe
445                 450                 455                 460

AAG CCT CAA CCT GTA GGT GTT TTT ACT CAT CAT GAT GTT GTT TAT GCA    1441
Lys Pro Gln Pro Val Gly Val Phe Thr His His Asp Val Val Tyr Ala
                465                 470                 475
```

FIG. 3F

```
CAA CAT TGT TTT AAA GCT CCC AAA AAT TTC TGT CCG TGT AAA TTG GAT    1489
Gln His Cys Phe Lys Ala Pro Lys Asn Phe Cys Pro Cys Lys Leu Asp
            480                     485                     490

GGG TCT TTG TGT GTA GGT AAT GGT CCT GGT ATA GAT GCT GGT TAT AAA    1537
Gly Ser Leu Cys Val Gly Asn Gly Pro Gly Ile Asp Ala Gly Tyr Lys
            495                     500                     505

AAT AGT GGT ATA GGC ACT TGT CCT GCA GGT ACT AAT TAT TTA ACT TGC    1585
Asn Ser Gly Ile Gly Thr Cys Pro Ala Gly Thr Asn Tyr Leu Thr Cys
            510                     515                     520

CAT AAT GCT GCC CAA TGT GAT TGT TTG TGC ACT CCC GAC CCC ATT ACA    1633
His Asn Ala Ala Gln Cys Asp Cys Leu Cys Thr Pro Asp Pro Ile Thr
            525                     530                     535                     540

TCT AAA TCT ACA GGG CCT TAC AAG TGC CCC CAA ACT AAA TAC TTA GTT    1681
Ser Lys Ser Thr Gly Pro Tyr Lys Cys Pro Gln Thr Lys Tyr Leu Val
            545                     550                     555
```

FIG. 3G

```
GGC ATA GGT GAG CAC TGT TCG GGT CTT GCT ATT AAA AGT GAT TAT TGT    1729
Gly Ile Gly Glu His Cys Ser Gly Leu Ala Ile Lys Ser Asp Tyr Cys
            560                 565                 570

GGA GGT AAT CCT TGT ACT TGC CAA CCA CAA GCA TTT TTG GGT TGG TCT    1777
Gly Gly Asn Pro Cys Thr Cys Gln Pro Gln Ala Phe Leu Gly Trp Ser
        575                 580                 585

GTT GAC TCT TGT TTA CAA GGG GAT AGG TGT AAT ATT TTT GCT AAT TTT    1825
Val Asp Ser Cys Leu Gln Gly Asp Arg Cys Asn Ile Phe Ala Asn Phe
        590                 595                 600

ATT TTT CAT GAT GTT AAT AGT GGT ACT ACT TGT TCT ACT GAT TTA CAA    1873
Ile Phe His Asp Val Asn Ser Gly Thr Thr Cys Ser Thr Asp Leu Gln
605                 610                 615                 620

AAA TCA AAC ACA GAC ATA ATT CTT GGT GTT TGT GTT AAT TAT GAT CTT    1921
Lys Ser Asn Thr Asp Ile Ile Leu Gly Val Cys Val Asn Tyr Asp Leu
        625                 630                 635
```

FIG. 3H

```
TAT GGT ATT ACA GGC CAA GGT ATT TTT GTT GAG GTT AAT GCG ACT TAT          1969
Tyr Gly Ile Thr Gly Gln Gly Ile Phe Val Glu Val Asn Ala Thr Tyr
            640                 645                 650

TAT AAT AGT TGG CAG AAC CTT TTA TAT GAT TCT AAT GGT AAT CTC TAT          2017
Tyr Asn Ser Trp Gln Asn Leu Leu Tyr Asp Ser Asn Gly Asn Leu Tyr
            655                 660                 665

GGT TTT AGA GAC TAC TTA ACA AAC AGA ACT TTT ATG ATT CGT AGT TGC          2065
Gly Phe Arg Asp Tyr Leu Thr Asn Arg Thr Phe Met Ile Arg Ser Cys
            670                 675                 680

TAT AGC GGT CGT GTT TCA GCG GCC TTT CAT GCT AAC TCT TCC GAA CCA          2113
Tyr Ser Gly Arg Val Ser Ala Ala Phe His Ala Asn Ser Ser Glu Pro
            685                 690                 695                 700

GCA TTG CTA TTT CGG AAT ATT AAA TGC AAT TAC GTT TTT AAT AAT ACT          2161
Ala Leu Leu Phe Arg Asn Ile Lys Cys Asn Tyr Val Phe Asn Asn Thr
            705                 710                 715
```

FIG. 3I

```
CTT TCA CGA CAG CTG CAA CCT ATT AAC TAT TTT GAT AGT TAT CTT GGT    2209
Leu Ser Arg Gln Leu Gln Pro Ile Asn Tyr Phe Asp Ser Tyr Leu Gly
        720                 725                 730

TGT GTC AAT GCT GAT AAT AGT ACT TCT AGT GTT GTT CAA ACA TGT        2257
Cys Val Asn Ala Asp Asn Ser Thr Ser Ser Val Val Gln Thr Cys
        735                 740                 745

GAT CTC ACA GTA GGT AGT GGT TAC TGT GTG GAT TAC TGT GTG GAT TAC TGT GTG GAT TAC    2305
Asp Leu Thr Val Gly Ser Gly Tyr Cys Val Asp Tyr Cys Val Asp Tyr Cys Val Asp Tyr
        750                 755                 760

CGA AGT CGT AGA GCG ATT ACC ACT GGT TAT CGG TTT ACT AAT TTT GAG    2353
Arg Ser Arg Arg Ala Ile Thr Thr Gly Tyr Arg Phe Thr Asn Phe Glu
765                 770                 775                 780

CCA TTT ACT GTT AAT GAT AGT GTA AAT GAT AGT TTA GAA CCT GTA GGT GGT    2401
Pro Phe Thr Val Asn Ser Val Asn Asp Ser Leu Glu Pro Val Gly Gly
                785                 790                 795
```

FIG. 3J

```
TTG TAT GAA ATT CAA ATA CCT TCA GAG TTT ACT ATA GGT AAT ATG GAG    2449
Leu Tyr Glu Ile Gln Ile Pro Ser Glu Phe Thr Ile Gly Asn Met Glu
             800                 805                 810

GAG TTT ATT CAA ACA AGC TCT CCT AAA GTT ACT ATT GAT TGT TCT GCT    2497
Glu Phe Ile Gln Thr Ser Ser Pro Lys Val Thr Ile Asp Cys Ser Ala
             815                 820                 825

TTT GTC TGT GGT GAT TAT GCA GCA TGT AAA TCA CAG TTG GTT GAA TAT    2545
Phe Val Cys Gly Asp Tyr Ala Ala Cys Lys Ser Gln Leu Val Glu Tyr
             830                 835                 840

GGT AGC TTC TGT GAC AAT ATT AAT GCT ATA CTC ACA GAA GTA AAT GAA    2593
Gly Ser Phe Cys Asp Asn Ile Asn Ala Ile Leu Thr Glu Val Asn Glu
             845                 850                 855                 860

CTA CTT GAC ACT ACA CAG TTG CAA GTA GCT AAT AGT TTA ATG AAT GGT    2641
Leu Leu Asp Thr Thr Gln Leu Gln Val Ala Asn Ser Leu Met Asn Gly
             865                 870                 875
```

FIG. 3K

```
GTC ACT CTT AGC ACT AAG CTT AAA GAT GGC GTT AAT TTC AAT GTA GAC    2689
Val Thr Leu Ser Thr Lys Leu Lys Asp Gly Val Asn Phe Asn Val Asp
            880                     885                     890

GAC ATC AAT TTT TCC CCT GTA TTA GGT TGT TTA GGA AGC GCT TGT AAT    2737
Asp Ile Asn Phe Ser Pro Val Leu Gly Cys Leu Gly Ser Ala Cys Asn
            895                     900                     905

AAA GTT TCC AGC AGA TCT GCT ATA GAG GAT TTA CTT TTT TCT AAA GTA    2785
Lys Val Ser Ser Arg Ser Ala Ile Glu Asp Leu Leu Phe Ser Lys Val
            910                     915                     920

AAG TTA TCT GAT GTC GGT TTC GTT GAG GCT TAT AAT AAT TGT ACT GGA    2833
Lys Leu Ser Asp Val Gly Phe Val Glu Ala Tyr Asn Asn Cys Thr Gly
            925                     930                     935                     940

GGT GCC GAA ATT AGG GAC CTC ATT TGT GTG CAA AGT TAT AAT GGT ATC    2881
Gly Ala Glu Ile Arg Asp Leu Ile Cys Val Gln Ser Tyr Asn Gly Ile
            945                     950                     955
```

FIG. 3L

```
AAA GTG TTG CCT CCA CTG CTC TCA GTA AAT CAG ATC AGT GGA TAC ACT          2929
Lys Val Leu Pro Pro Leu Leu Ser Val Asn Gln Ile Ser Gly Tyr Thr
             960                 965                 970

TTG GCT GCC ACC TCT GCT AGT CTG TTT CCT CCT TTG TCA GCA GCA GTA          2977
Leu Ala Ala Thr Ser Ala Ser Leu Phe Pro Pro Leu Ser Ala Ala Val
             975                 980                 985

GGT GTA CCA TTT TAT TTA AAT GTT CAG TAT CGT ATT AAT GGG ATT GGT          3025
Gly Val Pro Phe Tyr Leu Asn Val Gln Tyr Arg Ile Asn Gly Ile Gly
             990                 995                1000

GTT ACC ATG GAT GTG TTA AGT CAA AAT CAA AAG CTT ATT GCT AAT GCA          3073
Val Thr Met Asp Val Leu Ser Gln Asn Gln Lys Leu Ile Ala Asn Ala
            1005                1010                1015                1020

TTT AAC AAT GCT CTT GAT GCT ATT CAG GAA GGG TTT GAT GCT ACC AAT          3121
Phe Asn Asn Ala Leu Asp Ala Ile Gln Glu Gly Phe Asp Ala Thr Asn
            1025                1030                1035

FIG. 3M
```

```
TCT GCT TTA GTT AAA ATT CAA GCT GTT GTT AAT GCA AAT GCT GAA GCT      3169
Ser Ala Leu Val Lys Ile Gln Ala Val Val Asn Ala Asn Ala Glu Ala
           1040                    1045                    1050

CTT AAT AAC TTA TTG CAA CAA CTC TCT AAT AGA TTT GGT GCT ATA AGT      3217
Leu Asn Asn Leu Leu Gln Gln Leu Ser Asn Arg Phe Gly Ala Ile Ser
           1055                    1060                    1065

TCT TCT TTA CAA GAA ATT CTA TCT CTA TCT AGA CTG GAT GCT CTT GAA GCG CAA   3265
Ser Ser Leu Gln Glu Ile Leu Ser Leu Ser Arg Leu Asp Ala Leu Glu Ala Gln
        1070                    1075                    1080

GCT CAG ATA GAC AGA CTT ATT AAT GGG CGT CTT ACC GCT CTT AAT GTT      3313
Ala Gln Ile Asp Arg Leu Ile Asn Gly Arg Leu Thr Ala Leu Asn Val
           1085                    1090                    1095                    1100

TAT GTT TCT CAA CAG CTT AGT GAT TCT ACA CTA GTA AAA TTT AGT GCA      3361
Tyr Val Ser Gln Gln Leu Ser Asp Ser Thr Leu Val Lys Phe Ser Ala
           1105                    1110                    1115
```

FIG. 3N

```
GCA CAA GCT ATG GAG AAG GTT AAT GAA TGT GTC AAA AGC CAA TCA TCT    3409
Ala Gln Ala Met Glu Lys Val Asn Glu Cys Val Lys Ser Gln Ser Ser
            1120                    1125                    1130

AGG ATA AAT TTT TGT GGT AAT GGT AAT CAT ATT ATA TCA TTA GTG CAG    3457
Arg Ile Asn Phe Cys Gly Asn Gly Asn His Ile Ile Ser Leu Val Gln
            1135                    1140                    1145

AAT GCT CCA TAT GGT TTG TAT TTT ATC CAC TTT AGC TAT GTC CCT ACT    3505
Asn Ala Pro Tyr Gly Leu Tyr Phe Ile His Phe Ser Tyr Val Pro Thr
            1150                    1155                    1160

AAG TAT GTC ACT GCG AAG GTT AGT CCC GGT CTG TGC ATT GCT GGT GAT    3553
Lys Tyr Val Thr Ala Lys Val Ser Pro Gly Leu Cys Ile Ala Gly Asp
            1165                    1170                    1175                    1180

AGA GGT ATA GCC CCT AAG AGT GGT TAT TTT GTT AAT GTA AAT AAT ACT    3601
Arg Gly Ile Ala Pro Lys Ser Gly Tyr Phe Val Asn Val Asn Asn Thr
            1185                    1190                    1195
```

FIG. 30

```
TGG ATG TTC ACT GGT AGT GGT TAT TAC TAC CCT GAA CCC ATA ACT GGA    3649
Trp Met Phe Thr Gly Ser Gly Tyr Tyr Tyr Pro Glu Pro Ile Thr Gly
                1200                        1205                1210

AAT AAT GTT GTT GTT ATG AGT ACC TGT GCT GTT AAC TAT ACT AAA GCG    3697
Asn Asn Val Val Val Met Ser Thr Cys Ala Val Asn Tyr Thr Lys Ala
                1215                        1220                1225

CCG GAT GTA ATG CTG AAC ATT TCA ACA CCC AAC CTC CAT GAT TTT AAG    3745
Pro Asp Val Met Leu Asn Ile Ser Thr Pro Asn Leu His Asp Phe Lys
                1230                        1235                1240

GAA GAG TTG GAT CAA TGG TTT AAA AAC CAA ACA GTG GCA CCA GAT        3793
Glu Glu Leu Asp Gln Trp Phe Lys Asn Gln Thr Ser Val Ala Pro Asp
                1245                        1250                    1260
                                                                1255

TTG TCA CTT GAT TAT ATA AAT GTT ACA TTC TTG GAC CTA CAA GAT GAA    3841
Leu Ser Leu Asp Tyr Ile Asn Val Thr Phe Leu Asp Leu Gln Asp Glu
                1265                        1270                1275
```

FIG. 3P

```
ATG AAT AGG TTA CAG GAG GCA ATA AAA GTT TTA AAT CAG AGC TAC ATC    3889
Met Asn Arg Leu Gln Glu Ala Ile Lys Val Leu Asn Gln Ser Tyr Ile
        1280                    1285                    1290

AAT CTC AAG GAC ATT GGT ACA TAT GAG TAT TAT GTA AAA TGG CCT TGG    3937
Asn Leu Lys Asp Ile Gly Thr Tyr Glu Tyr Tyr Val Lys Trp Pro Trp
        1295                    1300                    1305

TAT GTA TGG CTT TTA ATT GGC TTT GCT GGT GTA GCT ATG CTT GTT TTA    3985
Tyr Val Trp Leu Leu Ile Gly Phe Ala Gly Val Ala Met Leu Val Leu
        1310                    1315                    1320

CTA TTC TTC ATA TGC TGT TGT ACA GGA TGT GGG ACT AGT TGT TTT AAG    4033
Leu Phe Phe Ile Cys Cys Cys Thr Gly Cys Gly Thr Ser Cys Phe Lys
        1325                    1330                    1335                    1340

ATA TGT GGT GGT TGT TGT GAT GAT TAT ACT GGA CAC CAG GAG TTA GTA    4081
Ile Cys Gly Gly Cys Cys Asp Asp Tyr Thr Gly His Gln Glu Leu Val
        1345                    1350                    1355
```

FIG. 3Q

```
ATT AAA ACA TCA CAT GAC GAC TAAGTTCGTC TTTGATTTAT TGGCTCCTGA        4132
Ile Lys Thr Ser His Asp Asp
               1360

CGATATATTA CATCCCTTCA ATCATGTGAA GCTAATTATA AGACCCATTG AGGTCGAGCA   4192

TATTATAATA GCTACCACAA TGCCTGCTGT TTAGTGGGTA CTGTGTCTTA TATAACTAGT   4252

AAACCTGTAA TGCCAATGGC TACAACCATT GACGGTACAG ATTATACTAA TATTATGCCT   4312

AGTACTGTTT CTACAACAGT TTATTTAGGC TGTTCTATAG GTA                     4355
```

FIG. 3R

ACTAAACTCA GTGAAA ATG TTT TTG CTT CTT AGA TTT GTT CTA GTT AGC   49
              Met Phe Leu Leu Arg Phe Val Leu Val Ser
               1                 5                  10

TGC ATA ATT GGT AGC CTA GGT TTT GAT AAC CCT CCT ACC AAT GTT GTT   97
Cys Ile Ile Gly Ser Leu Gly Phe Asp Asn Pro Pro Thr Asn Val Val
            15                  20                  25

TCG CAT TTA AAT GGA GAT TGG TTT TTA TTT GGT GAC AGT CGT TCA GAT  145
Ser His Leu Asn Gly Asp Trp Phe Leu Phe Gly Asp Ser Arg Ser Asp
        30                  35                  40

TGT AAT CAT GTT GTT AAT ACC AAC CCC CGT AAT TAT TCT TAT ATG GAC  193
Cys Asn His Val Val Asn Thr Asn Pro Arg Asn Tyr Ser Tyr Met Asp
    45                  50                  55

CTT AAT CCT GCC CTG TGT GAT TCT GGT AAA ATA TCA TCT AAA GCT GGC  241
Leu Asn Pro Ala Leu Cys Asp Ser Gly Lys Ile Ser Ser Lys Ala Gly
60                  65                  70                  75

FIG. 4A

```
AAC TCC ATT TTT AGG AGT TTT CAC TTT ACC GAT TTT TAT AAT TAC ACA    289
Asn Ser Ile Phe Arg Ser Phe His Phe Thr Asp Phe Tyr Asn Tyr Thr
             80                    85                    90

GGC GAA GGT CAA CAA ATT ATT TTT TAT GAG GGT CTT AAT TTT ACG CCT    337
Gly Glu Gly Gln Gln Ile Ile Phe Tyr Glu Gly Leu Asn Phe Thr Pro
             95                   100                   105

TAT CAT GCC TTT AAA TGC ACC ACT TCT GGT AGT AAT GAT ATT TGG ATG    385
Tyr His Ala Phe Lys Cys Thr Thr Ser Gly Ser Asn Asp Ile Trp Met
             110                  115                   120

CAC AAT AAA GGC TTG TTT TAC ACT CAG GTT TAT AAG AAT ATG GCT GTG    433
His Asn Lys Gly Leu Phe Tyr Thr Gln Val Tyr Lys Asn Met Ala Val
             125                  130                   135

TAT CGC AGC CTT ACT TTT GTT AAT GTA CCA TAT GTT TAT AAT GGC TCT    481
Tyr Arg Ser Leu Thr Phe Val Asn Val Pro Tyr Val Tyr Asn Gly Ser
             140                  145                   150              155
```

FIG. 4B

```
GCA CAA TCT ACA GCT CTT TGT AAA TCT GGT AGT TTA GTT CTT AAT AAC    529
Ala Gln Ser Thr Ala Leu Cys Lys Ser Gly Ser Leu Val Leu Asn Asn
            160                 165                 170

CCT GCA TAT ATA GCT CGT GAA GCT AAT TTT GGG GAT TAT TAT TAT AAG    577
Pro Ala Tyr Ile Ala Arg Glu Ala Asn Phe Gly Asp Tyr Tyr Tyr Lys
            175                 180                 185

GTT GAA GCT GAC TTT TAT TTG TCA GGT TGT GAC GAG TAT ATC GTA CCA    625
Val Glu Ala Asp Phe Tyr Leu Ser Gly Cys Asp Glu Tyr Ile Val Pro
            190                 195                 200

CTT TGT ATT TTT AAC GGC AAG TTT TTG TCG AAT ACA AAG TAT TAT GAT    673
Leu Cys Ile Phe Asn Gly Lys Phe Leu Ser Asn Thr Lys Tyr Tyr Asp
            205                 210                 215

GAT AGT CAA TAT TAT TTT AAT AAA GAC ACT GGT GTT ATT TAT GGT CTC    721
Asp Ser Gln Tyr Tyr Phe Asn Lys Asp Thr Gly Val Ile Tyr Gly Leu
            220                 225                 230                 235
```

FIG. 4C

```
AAT TCT ACT GAA ACC ATT ACC ACT GGT TTT GAT TTT AAT TGT CAT TAT    769
Asn Ser Thr Glu Thr Ile Thr Thr Gly Phe Asp Phe Asn Cys His Tyr
            240                 245                 250

TTA GTT TTA CCC TCT GGT AAT TAT TTA GCC ATT TCA AAT GAG CTA TTG    817
Leu Val Leu Pro Ser Gly Asn Tyr Leu Ala Ile Ser Asn Glu Leu Leu
            255                 260                 265

TTA ACT GTT CCT ACG AAA GCA ATC TGT CTT AAC AAG CGT AAG GAT TTT    865
Leu Thr Val Pro Thr Lys Ala Ile Cys Leu Asn Lys Arg Lys Asp Phe
            270                 275                 280

ACG CCT GTA CAG GTT GTT GAT TCA CGG TGG AAC AAT GCC AGG CAG TCT    913
Thr Pro Val Gln Val Val Asp Ser Arg Trp Asn Asn Ala Arg Gln Ser
            285                 290                 295

GAT AAC ATG ACG GCG GTT GCT TGT CAA CCC CCG TAC TGT TAT TTT CGT    961
Asp Asn Met Thr Ala Val Ala Cys Gln Pro Pro Tyr Cys Tyr Phe Arg
300                 305                 310                 315
```

FIG. 4D

```
AAT TCT ACT ACC AAC TAT GTT GGT GTT TAT GAT ATC AAT CAT GGG GAT    1009
Asn Ser Thr Thr Asn Tyr Val Gly Val Tyr Asp Ile Asn His Gly Asp
            320                 325                 330

GCT GGT TTT ACT AGC ATA CTC AGT GGT TTA TAT GAT TCA CCT TGT        1057
Ala Gly Phe Thr Ser Ile Leu Ser Gly Leu Tyr Asp Ser Pro Cys
        335                 340                 345

TTT TCG CAG CAA GGT GTT TTT AGG TAT GAT AAT GTT AGC AGT GTC TGG    1105
Phe Ser Gln Gln Gly Val Phe Arg Tyr Asp Asn Val Ser Ser Val Trp
            350                 355                 360

CCT CTC TAT TCC TAT GGC AGA TGC CCT ACT GCT GCT GAT ATT AAT ACC    1153
Pro Leu Tyr Ser Tyr Gly Arg Cys Pro Thr Ala Ala Asp Ile Asn Thr
            365                 370                 375

CCT GAT GTA CCT ATT TGT GTG TAT GAT CCG CTA CCA CTT ATT TTG CTT    1201
Pro Asp Val Pro Ile Cys Val Tyr Asp Pro Leu Pro Leu Ile Leu Leu
380                 385                 390                 395
```

FIG. 4E

```
GGC ATC CTT TTG GGT GTT GCG GTC ATA ATT ATT GTA GTT TTG TTG TTA    1249
Gly Ile Leu Leu Gly Val Ala Val Ile Ile Ile Val Val Leu Leu Leu
                400                 405                 410

TAT TTT ATG GTG GAT AAT GGT ACT AGG CTG CAT GAT GCT TAGACCATAA    1298
Tyr Phe Met Val Asp Asn Gly Thr Arg Leu His Asp Ala
            415                 420

TCTAAAC                                                            1305
```

FIG. 4F

```
BCV        M-FLILLISLPMAFAVIGDLKC-TTVSINDVDTGAPSISTDIVDVTNGLGTYYVLDRVYLN
JHM        MlFvfill-LPsclgyIGDfrCiqTVnyNgnnasAPSISTeaVDVskGrGTYVVLDRVYLN
A59        MlFvfilf-LPsslgyIGDfrCiqlVnsNganvsAPSISTetVeVsqGsGTYVVLDRVYLN 60        TTLLLNGYYPTSGSTYRNMALKGTLLLSRLWFKPPFLSDFINGIFAKVKNTKVIKKGVMYS
 61        aTLLLtGYYPvDGSnYRNlAltGTntLSltWFKPPFLSeFndGIFAKVqNlKtntptgats
 61        aTLLLtGYYPvDGSkfRNlAltGTnsvSlsWFqPPyLnqFndGIFAKVqNlKtdtpsgata 121        EFPAITIGSTFVNTSYSVVVQPHTNLDNKLQGLLEISVCQYTMCEYPHTICHPKL-GNKR
122        yFPtIvIGSLFgNTSYtVVlePynniimasvctyticqlp-YTpCk-PnTngn-rviGf--
122        yFPtIvIGSLFgyTSYtVViePyngvimasvcqyticqlp-YTdCk-PnTngn-KLiGf--

181        VSLWHWDTGVVSCLYKRNFTYDVNADY-YFHFYQEGSTFYAYFTDTGVVTKFLFNVYLGT--
178        ---WHtDvkppiCLlKRNFTfnVNApwLYFHFYQgGGTFYAYaDkpsaTtFLFsVYigdiktqyf
178        ---WHtDvkppiCVlKRNFTlnVNADafYFHFYQhGGTFYAYaDkpsaTtFLFsVYigdilyqyy 241        VLSHYYVLPLTCSSAMTLEYWVTPLTSKQYLLAFNQDGVIFNAVDCKSDFMSEIKCKTLS
241        VL-pfictPtagStlapL-YWVTPLlkrQYLfnFNekGVITsAVDCaSsyiSEIKCKTqS
241        VL-pficnPtagStfapr-YWVTPLvkrQYLfnFNQkGVITsAVDCaSsytSEIKCKTqS
```

FIG. 8A

```
301  IAPSTGVYELNGYTVQPIADVYRRIPNLPDCNIEAWLNDKSVPSPLNWERKTFSNCNFNMSS
299  llPSTGVYdLsGYTVQPvgvVYRRvPNLPDCkIEeWLtaKSVPSPLNWERrTFqNCNFNlsS
299  mlPSTGVYELsGYTVQPvgvVYRRvaNLPaCNIEeWLtarSVPSPLNWERKTFqNCNFNlsS 363  LMSFIQADSFTCNNIDAAKIYGMCFSSITIDKFAIPNGRKVDLQLGNLGYLQSFNYRIDT
361  LlryvQAeSlsCNNIDAsKvYGMCFgSvsvDKFAIPrsRqiDLQIGNsGflQtaNYKIDT
361  LlryvQAeSlfCNNIDAsKvYGRCFgSIsvDKFAvPrsRqVDLQLGNsGflQtaNYKIDT 423  TATSCQLYYNLPAANVSVSRFNPSTWNRRFGFTEQFVF-KPQPVGVFTHHDVVYAQHCF
421  aATSCQLYYsLPknNVtinnyNPSsWNRRYGFkvn------------------
421  aATSCQLhYtLPknNVtinnhNPSsWNRRYGFndagVFgKnQ------HDVVYAQqCF 481  KAPKNFCPCKL-D-GSLCVGNGPGIDAEYKNSGIGTCPAGTNYLTCHNAAQCDCLCTPDPIT
473  tvrcsyCPCaqpDivSpCt------------------------------

541  SKSTGPYKCPQTKYL---VGIGEHCSGLAIKSDYCGG-NP---CTCQPQAFLGWSVDSCLQSDRCN
456  ----------------------------------------------------DRCq
493  ------tQTKpksafVnvgdHCeGLgvleDnCgnadPhkgCiCannsFiGWShDtCLvnDRCq
```

FIG. 8B

```
601  FANFIFHDVNSGTTCSTDLQKSNTDIILGVCVNYDLYGITGQGIFVEVNATYYNSWQNLL
461  FANilnginSGTTCSTDLQlpNTevatGVCVrYDLYGITGQGvFkEVkAdYYNSWQaLL
550  FANilnginSGTTCSTDLQlpNTavvtGiCVkYDLYGITGQGvFkEVkAdYYNSWQtLL 661  YDSNGNLYGFRDYLTNRTFMIRSCYSGRVSAAFHANSSEPALLFRNIKCNYVFNNTLSRQ
521  YDSNGNLnGFRDltTNkTytIRSCYSGRVSAAyHkeaPEPALLyRNIncSYVFtNniSRe
610  YDvNGNLnGFRDltTNkTytIRSCYSGRVSAAFHkdaPEPALLyRNIkCsYVFsNniSRe 721  LQPINYFDSYLGCVVNADNSTSSVVQTCDLTVGSGYCVDYSTKRRSRRAITTGYRFTNFE
581  enPlNYFDSYLGCVVNADNrTdealpnCnLrmGaGLCVDYSksRRaRRsvsTGYRlTfFE
670  enPlNYFDSYLGCVVNADNrTdealpnCDLrmGaGLCVDYSksRRahRsvsTGYRlTfFE 781  PFTVNSVNDSLEPVGGLYEIQIPSEFTIGNMEEFIQTSSPKVTIDCSAFVCGDYAACKSQ
641  PympmlVNDSLqsVGGLYEmQIPtnFTIGhhEEFIQiraPKVTIDCaAFVCGDnAACrqQ
730  PyTpmlVNDSvqsVdgLYEmQIPtnFTIGhhEEFIQTrSPKVTIDCaAFVCGDntACrqQ 841  LVEYGSFCDNINAILTEVNELLDTTQLQVANSLMNGVTLSTKLKDGVNFNVDDINFSPVL
701  LVEYGSFCDNvNAILnEVNnLLDnmQLQVAsaLMgGVTiSsrLpDGisgpiDDINFSPlL
790  LVEYGSFCVNvNAILnEVNnLLDnmQLQVAsaLMgGVTiSsrLpDGisgpiDDINFSPlL
```

FIG. 8C

```
901   GCLGSAC-----NKVSS---RSAIEDLLFSKVKLSDVGFVEAYNNCTGGAEIRDLICVQSYNGIKVL
751   GCIGStCaedgNgpSairgRSAIEDLLFdKVKLSDVGFVEAYNNCTGGqEVRDLICVQSfNGIKVL
850   GCIGStCaedgNgpSairgRSAIEDLLFdKVKLSDVGFVEAYNNCTGGqEVRDLICVQSfNGIKVL 961   PLLSVNQISGYTLAATSASLFPPLSAAVGVPFYLNVQYRINGIGVTMDVLSQNQKLIANA
828   PvlSesQISGYTagaTaAamFPPwtAAaGVPFsLNVQYRINGlGVTMnVLSeNQKmIAsA
917   PvLSesQISGYTtgATaAamFPPwSAAaGVPFsLsVQYRINGlGVTMnVLSeNQKmIAsA 1021  FNNALDAIQEGFDATNSALVKIQAVVNANAEALNNLLQQLSNRFGAISSSLQEILSRLDA
888   FNNALgAIQEGFDATNSALgKIQsVVNANAEALNNLLnQLSNRFGAISaSLQEILSRLDA
977   FNNALgAIQDGFDATNSALgKIQsVVNANAEALNNLLnQLSNRFGAISaSLQEILTRLEA 1081  LEAQAQIDRLINGRLTALNVVSQQLSDSTLVKFSAAQAMEKVNECVKSQSSRINFCGNG
948   VEAkAQIDRLINGRLTALNaYiSkQLSDSTLiKFSAAQAiEKVNECVKSQtTRINFCGNG
1037  VEAkAQIDRLINGRLTALNaYiSkQLSDSTLiKVSAAQAiEKVNECVKSQtTRINFCGNG 1141  NHIISLVQNAPYGLYFIHFSYVPTKYVTAKVSPGLCIAGDRGIAPKSGYFVNVNNTWMFT
1008  NHIlSLVQNAPYGLCFIHFSYVPTsfKTAnVSPGLCIsGDRGlAPKaGYFVqdNgeWKFT
1097  NHIISLVQNAPYGLYFIHFSYVPIsfTAnVSPGLCIsGDRGlAPKaGYFVqddgeWKFT
```

FIG. 8D

```
1201  GSGYYYPEPITGNNVVVMSTCAVNYTKAPDVMLNISTPNLHDFKEELDQWFKNQTSVAPD
1068  GSnYYYPEPITdkNsVaMisCAVNYTKAPeVfLNnsiPNLpDFKEELDkWFKNQTSiAPD
1157  GSsYYYPEPITdkNsViMSsCAVNYTKAPeVfLNtsiPNPpDFKEELDkWFKNQTSiAPD 1261  LSLDY--INVTFLDLQDEMNRLQEAIKVLNQSYINLKDIGTYEYYVKWPYVWLLIGFASVA
1120  LSLDfeklNVTFLDLtyEMNRiQdAIKkLNaSYINLKevGTYEmYVKWPYVWLLIGLAGVA
1217  LSLDfwklNVTlLDLtyEMNRiQdAIKkLNeSYINLKevGTYEmYVKWPYVWLLIGLAGVA 1321  MLVLFFICCCTGCGTSCFKICGGCCDDYTGHQE-LVIKT-S-HDD
1190  vCVLLFFICCCTGCGScCFRkCGSCCDeYgGHQdsiVIhniSaHeD
1278  vCVLLFFICCCTGCGScCFKkCGnCCDeYgGHQesiVIhnisSHeD
```

FIG. 8E

RECOMBINANT BOVINE CORONAVIRUS EZ AND E3 POLYPEPTIDES AND VACCINES

CROSS-REFERENCE TO RELATED APPLICATIONS

This application is a continuation of application Ser. No. 07/811,422, filed Dec. 19, 1991 (now abandoned) which is a CIP of Ser. No. 07/779,500 filed Oct. 18, 1991 (now abandoned) which is a CIP of Ser. No. 07/397,689 filed Aug. 22, 1989 (now abandoned).

TECHNICAL FIELD

The present invention is directed to vaccines to protect against coronavirus infection, with particular usefulness in protecting cattle against bovine coronavirus ("BCV"). The present invention is also directed to the materials and methods for producing coronavirus vaccines, as well as methods of using the vaccines.

BACKGROUND OF THE INVENTION

Coronaviruses were initially recognized as a unique group based on their distinctive morphology. The virions, when negatively stained, have large, petal-shaped glycoprotein spikes or "peplomers." These spikes project from the envelope of the virions. The name "coronavirus" was suggested because of the virus' resemblance to the corona spinarium, or crown of thorns, that surrounded the heads of figures in medieval religious art. Alternatively, the appearance of the projecting proteins of the virion has been likened to the solar corona.

The coronaviruses cause diseases in humans as well as in domestic and laboratory animals. Many of these diseases are of great economic importance, often causing severe enteric or respiratory infection in animals. Characteristically, the coronaviruses which cause enteric infections result in only mild or inapparent infection in adult animals, but cause severe diarrheal disease in newborn or infant animals.

The coronavirus has several structural components. Its genomic RNA is a single plus strand that is 28 to 31 kilobases long. The coronaviruses are enveloped RNA viruses. Thus, the nucleocapsid lies within a lipoprotein envelope. This envelope is derived from either the rough endoplasmic reticulum or the Golgi apparatus of infected cells. Within the lipid bilayer of the envelope are other viral glycoproteins.

The coronaviruses comprise at least four antigenic groups. These groups have been characterized based on enzyme-linked immunoassays (ELISA), serologic studies with immunofluorescence assays, virus-neutralization tests, and immunoelectron microscopy. Within each group, the viruses exhibit partial antigenic cross-reactivity; they are, however readily distinguished by their host specificity and clinical syndromes.

Coronaviruses usually have three unique, major structural proteins: N, E1 (or "M"), and E2 (or "S"). In addition, some coronaviruses, such as bovine coronavirus, have a fourth structural protein designated E3 (or "HE").

The N or nucleocapsid protein is a basic phosphoprotein of 50 to 60K. Many copies of the N protein combine with the genomic RNA to form a long, flexible nucleocapsid having helical symmetry. The N protein is the most abundant protein in the virion. The N proteins of porcine transmissible gastroenteritis virus (TGEV), mouse hepatitis virus (MHV), and avian infectious bronchitis virus (IBV) show only about 27% homology with each other.

The transmembrane or matrix protein, designated E1 (the name for which has officially been changed to "M"), is often a group of differently glycosylated proteins including a nonglycosylated precursor. The E1 protein serves to bind the nucleocapsid to the viral envelope as the virus buds into the endoplasmic reticulum and Golgi apparatus membranes. E1 may be phosphorylated on serine or threonine residues rather than on asparagine as are most other viral glycoproteins. Antibodies to E1 require the presence of complement to neutralize viral infectivity.

The peplomer protein, often designated E2, but which has officially been changed to "S", is a glycoprotein that makes up the large "petal shaped" surface projections of the virus. A small anchor of the protein is embedded in the membrane, with most of the molecule residing outside of the lipid bilayer. E2 has an apparent molecular weight of 180 to 200K. The E2 glycoprotein is involved in virus attachment, cell membrane fusion, and virus-neutralizing antibody production.

The E2 proteins of FIPV and the closely-related TGEV differ from E2 of MHV and IBV in two important respects. First, proteolytic cleavage of E2 is not required for activation; FIPV is effective in inducing cell fusion. Second, the E2 of FIPV and TGEV are larger (210K compared to 180K, with proteolytic cleavage to two products of 80 to 90K required for cell fusion activity in MHV). In addition, de Groot et al., (1987) Adv, Exp. Med. Biol. 218:31–38, report that the cloning and sequencing of the E2 genes of IBV M41, MHVA59 and FIPV 79–1146 indicated that the E2 proteins have low overall amino acid homology (with no numerical percentage given; regions were considered highly homologous if two sequences were at least 30% identical).

Infectious Bronchitis Virus (IBV) Avian:

Infectious bronchitis virus (IBV) avian is a respiratory pathogen in fowl and therefore of great economic importance to the poultry industry. Background IBV (M41) E2 characterization my be found in Cavanagh (1983), J. Gen. Virology 64:2577–2583.

Cavanagh et al., (1984) Avian Pathology 13:573–583, reported inoculating chickens with sucrose gradient purified IBV proteins and then challenging the inoculated birds with IBV. Although E2 (termed "S" for spike by the Cavanagh lab) caused antibody production, it was ineffective to impart IBV protection/resistance to the inoculated chickens, as evidenced by their susceptibility to the characteristic IBV respiratory infection.

Mockett et al. (1984), J. Gen. Virology 65:2281–2286, have produced anti-E2 monoclonal antibodies (MAbs) which neutralized only one strain of IBV (M41) in vitro.

Tomley et al. (1987), J. Gen. Virology 68:2291–2298, have made a cDNA clone of IBV E2 and inserted it into a vaccinia virus. The expressed recombinant E2 protein was recognized by anti-E2 antisera. Mice were vaccinated with the recombinant virus. The neutralization titers of inoculated mice, although higher than the controls, were, however, low. (7 weeks after inoculation, mice injected with the recombinant virus had a neutralization titer of 1:25 against the test strain compared to 1:10 for sera from mice inoculated with control (wild type vaccinia) virus.)

According to one source, "excellent vaccines are available for IBV" but "the disease is still widespread due to the occurrence of new variants." Niesters et al., (1986) Virus Research 5:253–263, at 261. The authors, therefore, synthesized cDNA clones, reported the IBV M41 nucleotide sequence and compared the predicted amino acid sequences of two IBV strains (M41 and M42), which have different neutralization epitopes in an attempt to localize the IBV neutralizing epitopes. Niesters et al., (1986), supra, at 257, FIG. 2. The authors stated that "[s]o far as is known, only antibodies directed against the S1 [portion] of the peplomer protein are able to neutralize virus infectivity." Niesters et al., supra, at 261. Tomley et al., supra, reiterated that no other viral proteins are targets for antibody-mediated virus neutralization. "Despite this [knowledge], protective immune responses have not yet been obtained in birds inoculated with purified spike protein." Tomley et al. at 2292.

Porcine Transmissible Gastroenteritis (TGEV)

Porcine transmissible gastroenteritis (TGEV) causes neonatal viral enteritis. Infection is often fatal for piglets under two weeks of age. TGEV, like the murine and avian coronaviruses, has the three polypeptides N, E1, and E2. Anti-E2 monoclonal antibodies were generated (using a concentrated crude suspension of Purdue virus) and used in in vitro neutralization assays. Laude et al. (1986), J. Gen. Virology 67:119–130.

Mouse Hepatitis Virus (MHV)

Mouse hepatitis virus (MHV) is a neurotropic virus which has been studied quite extensively; since it causes demyelination, MHV is a possible model for such diseases as multiple sclerosis. Sturman et al. (1985), J. Virology 56:904–911, report that coronavirus infection frequently results in cell fusion both in vivo and in vitro. In vitro, the syncytia detach from the substrate and die. Monospecific serum to E2 added to cell cultures 2–4 hours after inoculation was shown to "markedly inhibit" cell fusion. Furthermore, it was reported that proteolytic cleavage of E2 may be required to initiate or activate the cell-fusing activity of the protein.

MHV-4, JHM strain is also reported to contain the three major structural proteins N, E1, and E2. Dalziel et al. (1986), J. Virology 59:463–471, at 463. Dalziel et al. prepared anti-E2 MAbs and studied the effect of mutation on virulence. Virus neutralization by the MAbs was evaluated in vitro. Earlier work by this laboratory, reported in Talbot et al., (1984), Virology 132:250–260, identified four epitopes on E2, two of which mediated virus neutralization in vitro. Anti-E2 MAbs passively protected mice from lethal challenge to intracerebral inoculation with MHV-4 in vivo, although they still suffered demyelination. Buchmeier et al. (1984), Virology 132:261–270. The studies by Buchmeier et al. point out that in vitro neutralization and in vivo protection are not correlated. Buchmeier et al., supra, at 268, col. 1. Infection of the central nervous system by MHV was not prevented by those MAbs designated "protective." Protection apparently was conferred by slowing of viral replication, without stopping it. Id. In addition, "protective" antibody, which protected against lethal encephalitis, did not prevent demyelination by a MHV-4 temperature-sensitive mutant. Id. at 269, col. 1.

Wege et al. (1984), J. Gen. Virology 65:1931–1942, also studied the ability of anti-E2 MAbs to protect rats from acute encephalomyelitis (Table 3, at 1939). Wege et al. developed and analyzed monoclonal antibodies against various epitopes of MHV E2 protein. Some of the antibodies which inhibited cell fusion in vitro were able to prevent rats from developing fatal encephalomyelitis, although demyelination was not eliminated but was merely reduced. Again, passive protection against lethal challenge using MAbs to MHV E2 provides limited protection in the murine system as shown by both Dalziel et al. supra, and the Wege group. Schmidt et al., (1987) J. Gen. Virology 68:47–56, have sequenced E2 and predicted the amino acid sequence. The S2 subunit of E2, is presumed to remain membrane-bound following proteolytic cleavage/cell-fusing activation. This is somewhat similar to the S2 subunit of IBV. Makino et al. (1987), Proc. Natl. Acad. Sci. 84:6567–6571, reported that the carboxy terminal 1/3 of E2 is at least partially responsible for MHV neuropathogenicity and neutralization and postulated that cleavage of the 180K E2 protein to 90K subunits, which activates cell-fusion, may expose the carboxyl half of E2; these results, however, have since been refuted.

The field of coronavirus research has been principally directed to the murine virus system due to the potential for understanding diseases of the nervous system. In addition, research on the avian IBV and the porcine TGEV have been of great interest to the poultry and the swine industries, respectively. In these non-BCV coronavirus systems, the development of vaccines appears to have been limited to the poultry industry; due to the development of new variants, however, IBV disease is still widespread. Niesters et al., supra. Early studies have been done on eliciting passive protection to MHV.

Bovine coronavirus (BCV) is an important virus in the cattle industry. BCV research has been directed to developing cell lines for production and isolation of BCV from cell cultures. Dea et al. (1980), Am. J. Vet. Res. 41:30–38. In addition, one research group has used whole virus to produce antisera, identifying various glycoproteins. King et al. (1982), J. Virology 42:700–707; Hogue et al. (1984), J. Virology 51:384–388; King et al. (1985), Virus Research 2:53–59. This group has also mapped the BCV Mebus strain genes which encode N and E1 (called "M" for matrix). Lapps et al., (1987) Virology 157:47–57. Hogue et al., (1984), supra, used immunoblots to identify a gp140 (glycoprotein having molecular weight of 140K) composed of disulfide-linked 65K subunits. King et al., (1985), supra, have also reported a 140K glycoprotein, which is a disulfide-linked dimer of two 65K glycoproteins, which they state is the hemagglutinating protein of BCV. Other than its function as a hemagglutinin, its role in BCV replication and pathogenesis are reported as unknown. The glycoproteins identified by this group have not been confirmed or reproduced by other groups. The proteins identified could be fragments or artifacts of the various native BCV proteins. Development of BCV vaccines has not been reported.

The BCV E2 glycoprotein has an apparent molecular weight of 190K which may presumably be cleaved to two comigrating 100K proteins. [S protein by convention is cleaved into two pieces, S1 and S2, representing the amino and carboxy terminus, respectively.] The precursor to E2 is a 170K glycoprotein. This 170K precursor appears to be further glycosylated to yield the 190K E2 (Deregt, D., and Babiuk, L., (1987) Virology 161:410–420).

E3 (which has officially been renamed "HE") is unique to certain coronaviruses. These include bovine coronavirus, the hemagglutinating encephalomyelitis virus (HEV) of swine, and the human respiratory coronavirus (HCV-OC43). See, e.g., Parker et al. (1989) J. Gen. Virol. 70:155–64.

An ideal BCV vaccine would have the ability to protect or ameliorate pathogenesis without the risk of infection, a risk which exists with a live or whole virus vaccine.

DISCLOSURE OF THE INVENTION

In the present invention, it has been discovered that BCV has, in addition to the E2 protein, a protein designated "E3." Recombinant BCV polypeptides have been produced from cloned E2 and E3 genes. The E2 and E3 genes have been sequenced and the amino acid sequence of the primary translation product of these genes has been predicted. The BCV E2 and E3 glycoproteins, particularly the recombinant form of these proteins, have been identified as important immunological targets and therefore useful as components of a vaccine directed toward preventing BCV infection in bovine populations. The recombinant E2 and E3 of the present invention are very effective subunit antigens for a vaccine composition. Further, clones which represent the entire BCV genome have been constructed and the E2 and E3 gene sequences have been identified.

The present invention, therefore, has several embodiments. In particular, the invention is directed to a DNA molecule comprising a coding sequence for BCV protein or antigenic fragments thereof, wherein the BCV protein is selected from the group consisting of E2 and E3. Identification of antigenic fragments is within the skill of the art in view of the disclosure herein and includes, for example, producing trypsin fragments, short oligopeptides, etc., and using standard methods to screen the fragments produced for antigenicity and other activity. The DNA molecule may further comprise an expression cassette comprising the above coding sequence and control sequences operably linked to the coding sequence whereby the coding sequence can be transcribed and translated in a host cell, wherein at least one of the control sequences is heterologous to the coding sequence. The coding sequence may encode substantially complete BCV protein, such as E2 and/or E3, or antigenic fragments of E2 and/or E3.

The present invention is also directed to host cells comprising this DNA molecule, as well as methods of producing recombinant polypeptides comprising an antigenic BCV E2 or E3 sequences.

In another embodiment, the present invention is directed to a method of eliciting an immune response in a mammalian host against BCV infection comprising: (a) providing a vaccine composition comprising a pharmaceutically acceptable carrier and at least one subunit antigen comprising an antigenic BCV polypeptide selected from the group consisting of E2, E3, and antigenic fragments thereof; and (b) administering to the mammalian host an amount of the vaccine composition effective to elicit an immune response.

In yet another embodiment of the present invention, a vaccine composition for (BCV) is provided comprising a pharmaceutically acceptable vehicle and an effective amount of antigenic BCV polypeptide.

Yet another embodiment of the present invention is a composition comprising substantially pure Bovine Coronavirus (BCV) polypeptide or antigenic fragments thereof wherein the BCV protein is selected from the group consisting of E2 and E3.

The following disclosure will render these and other embodiments of the present invention readily apparent to those of skill in the art.

BRIEF DESCRIPTION OF THE DRAWINGS

FIG. 3 shows the BCV E2 gene nucleotide sequence and the predicted amino acid sequence of the E2 precursor protein. Reference numbers for the polynucleotides are located above the sequence with asterisks used to indicate the precise positioning of the nucleotide corresponding to the reference number. Reference numbers for the amino acid sequence appear at the right-hand side end of each line. The conserved intergenic sequence is surrounded by a rectangle; the amino-terminal signal sequence is underscored with a solid line; the carboxy-terminal transmembrane domain is underscored with a discontinuous line; an arrow indicates a probable site of precursor cleavage, and potential N-linked glycosylation sites are indicated by solid circles.

FIG. 4 shows the BCV E3 gene nucleotide sequence and the predicted amino acid sequence of the primary translation product. Reference numbers for the polynucleotides are located above the sequence with asterisks used to indicate the precise position of the nucleotide corresponding to the reference number. Reference numbers for the amino acid sequence appear at the right-hand side end of each line. The conserved intergenic sequence is surrounded by a rectangle; the amino-terminal signal sequence is underscored with a solid line; the carboxy-terminal transmembrane domain is underscored with a solid line passing through open circles, and potential N-linked glycosylation sites are indicated by solid circles.

FIG. 8 is a comparison of the amino acid sequence homology between E2 glycoproteins of bovine coronavirus and murine hepatitis virus strains JHM and A59. (JHM from Schmidt et al. (1987) *J. General Virology* 68:47–56; A59 is from deGroot et al. (1987) *Adv. Exp. Med. Biol.* 218:31–38.)

MODES OF CARRYING OUT THE INVENTION

The practice of the present invention will employ, unless otherwise indicated, conventional microbiology, virology, molecular biology, and recombinant DNA techniques which are within the skill of the art. These techniques are fully explained in the literature. See, e.g., Maniatis et al., *Molecular Cloning: A Laboratory Manual* (1982); *DNA Cloning: A Practical Approach*, vols. I & II (D. Glover, ed.); *Oligonucleotide Synthesis* (N. Gait, ed. (1984)); *Nucleic Acid Hybridization* (B. Hames & S. Higgins, eds. (1985)); *Transcription and Translation* (B. Hames & S. Higgins, eds. (1984)); *Animal Cell Culture* (R. Freshney, ed. (1986)); Perbal, *A Practical Guide to Molecular Cloning* (1984).

A. Definitions

In describing the present invention, the following terminology, as defined below, will be used.

A "replicon" is any genetic element (e.g., plasmid, chromosome, virus) that functions as an autonomous unit of DNA replication in vivo; i.e., is capable of replication under its own control.

A "vector" is a replicon, such as a plasmid, phage, or cosmid, to which another DNA segment may be attached so as to bring about the replication of the attached segment.

A "double-stranded DNA molecule" refers to the polymeric form of deoxyribonucleotides (adenine, guanine, thymine, or cytosine) in its normal, double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having the sequence homologous to the mRNA).

A DNA "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, and even synthetic DNA sequences. A polyadenylation signal and transcription termination sequence will usually be located 3' to the coding sequence.

A "promoter sequence" is a DNA regulatory region capable of binding RNA polymerase in a cell and initiating transcription of a downstream (3' direction) coding sequence. For purposes of defining the present invention, the promoter sequence is bound at the 3' terminus by the translation start codon (ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eucaryotic promoters will often, but not always, contain "TATA" boxes and "CAT" boxes. Procaryotic promoters contain Shine-Dalgarno sequences in addition to the −10 and −35 consensus sequences.

DNA "control sequences" refer collectively to promoter sequences, ribosome binding sites, polyadenylation signals, transcription termination sequences, upstream regulatory domains, enhancers, and the like, which collectively provide for the transcription and translation of a coding sequence in a host cell.

A coding sequence is "operably linked to" or "under the control of" control sequences in a cell when RNA polymerase will bind the promoter sequence and transcribe the coding sequence into mRNA, which is then translated into the polypeptide encoded by the coding sequence.

A "host cell" is a cell which has been transformed, or is capable of transformation, by an exogenous DNA sequence.

A cell has been "transformed" by exogenous DNA when such exogenous DNA has been introduced inside the cell membrane. Exogenous DNA may or may not be integrated (covalently linked) to chromosomal DNA making up the genome of the cell. In procaryotes and yeasts, for example, the exogenous DNA may be maintained on an episomal element, such as a plasmid. A stably transformed cell is one in which the exogenous DNA has become integrated into the chromosome so that it is inherited by daughter cells through chromosome replication. For mammalian cells, this stability is demonstrated by the ability of the cell to establish cell lines or clones comprised of a population of daughter cell containing the exogenous DNA.

A "clone" is a population of daughter cells derived from a single cell or common ancestor. A "cell line" is a clone of a primary cell that is capable of stable growth in vitro for many generations.

Two polypeptide sequences are "substantially homologous" when at least about 80% (preferably at least about 90%, and most preferably at least about 95%) of the amino acids match over a defined length of the molecule.

Two DNA sequences are "substantially homologous" when they are identical to or not differing in more that 40% of the nucleotides, more preferably about 20% of the nucleotides, and most preferably about 10% of the nucleotides.

DNA sequences that are substantially homologous can be identified in a Southern hybridization experiment under, for example, stringent conditions, as defined for that particular system. Defining appropriate hybridization conditions is within the skill of the art. See, e.g., Maniatis et al., supra; *DNA Cloning*, vols. I & II, supra; *Nucleic Acid Hybridization*, Supra.

A "heterologous" region of a DNA construct is an identifiable segment of DNA within or attached to another DNA molecule that is not found in association with the other molecule in nature. Thus, when the heterologous region encodes a viral gene, the gene will usually be flanked by DNA that does not flank the viral gene in the genome of the source virus or virus-infected cells. Another example of the heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

Figure 1:
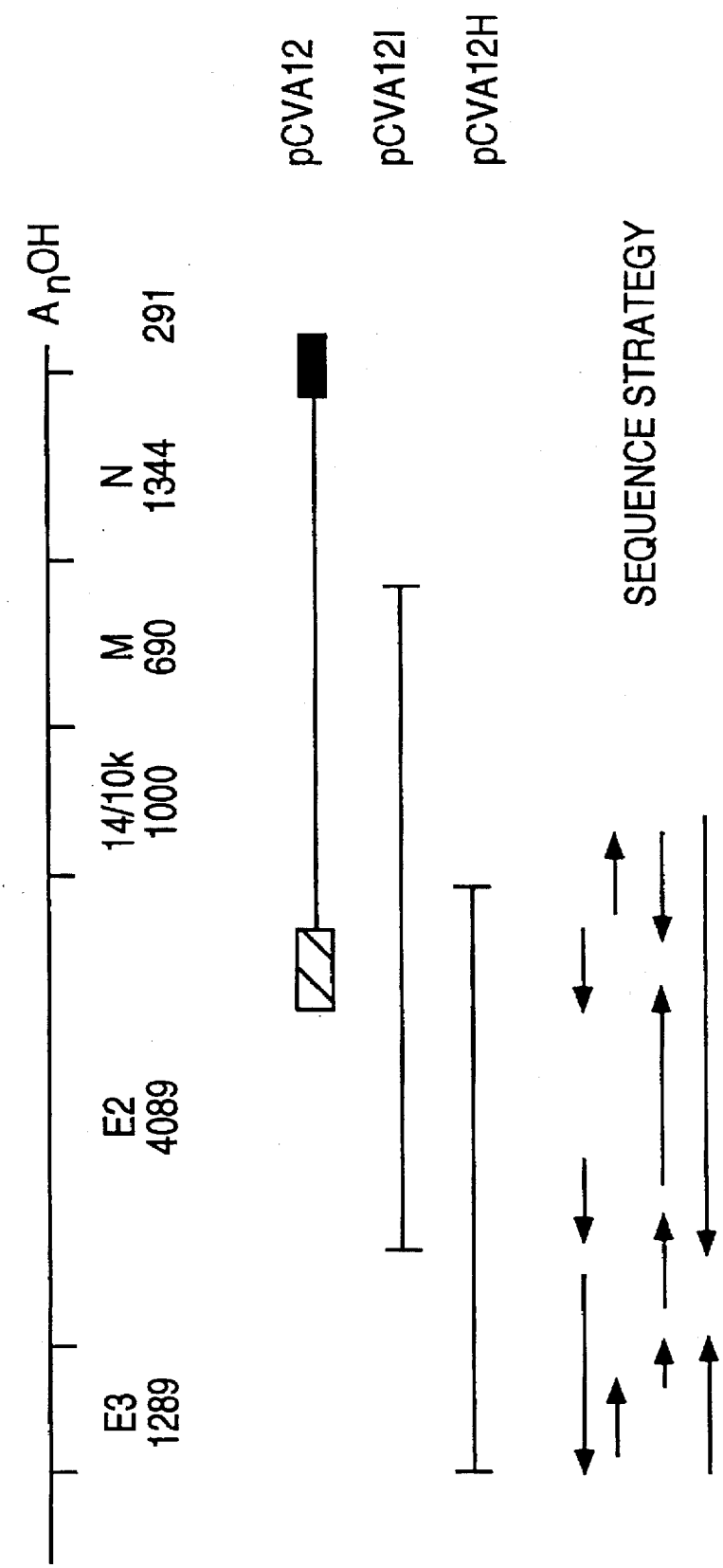
FIG. 1 is a schematic genetic map of BCV structural protein genes. Approximately 10,000 nucleotides of the viral genome are represented in the figure. The length of the reading frame of each gene is indicated in nucleotides with the number of nucleotides appearing below the name for each gene. The length of the BCV N gene and 3' non-coding region are from Lapps et al. Also shown is pCVA12 probe homologous to the 3' end of the viral genome with 5' portion of pCVA12 used to identify clones extending into the E2 gene.

"Bovine host" refers to cattle of any breed.

The term "protein" or "glycoprotein" is used herein to designate a polypeptide or glycosylated polypeptide, respectively. The term "polypeptide" is used in its broadest sense, i.e., any polymer of amino acids (dipeptide or greater) linked through peptide bonds. Thus, the term "polypeptide" includes proteins, oligopeptides, protein fragments, analogs, muteins, fusion proteins and the like.

"Fusion protein" is usually defined as the expression product of a gene comprising a first region encoding a leader sequence or a stabilizing polypeptide, and a second region encoding a heterologous protein. It involves a polypeptide comprising an antigenic protein fragment or a full length BCV protein sequence as well as (a) heterologous sequence (s), typically a leader sequence functional for secretion in a recombinant host for intracellularly expressed polypeptide, or an N-terminal sequence that protects the protein from host cell proteases, such as SOD. An antigenic protein fragment is usually about 5–7 amino acids in length.

"Native" proteins or polypeptides refer to proteins or polypeptides recovered from BCV or BCV-infected cells. Thus, the term "native BCV polypeptide" would include naturally occurring BCV proteins and fragments thereof. "Non-native" polypeptides refer to polypeptides that have been produced by recombinant DNA methods or by direct synthesis. "Recombinant" polypeptides refers to polypeptides produced by recombinant DNA techniques; i.e., produced from cells transformed by an exogenous DNA construct encoding the desired polypeptide.

"BCV protein" means a polypeptide having a sequence substantially homologous to a native BCV protein.

A "substantially pure" BCV protein will be free of other BCV proteins, preferably at least 10% homogeneous, more preferably 60% homogeneous, and most preferably 95% homogeneous.

A "subunit antigen" is an antigen separate from a whole virus or virus-infected cell. For example a subunit antigen may be a recombinant protein and, in the preferred embodiment, can also comprise naturally occurring antigen isolated from whole virus, virus lysate, or infected cells.

B. General Method

Bovine Coronavirus (BCV) is a well-known virus, and has a single-stranded, nonsegmented, polyadenylated RNA genome of approximately 20 kb (Lapps et al., (1987) *Virology* 157:47–57). BCV is composed of the proteins N, E1, and E2. In addition, it has been discovered that BCV has a fourth structural protein, designated E3, which has now been cloned and characterized. Particularly important to the present invention are the E2 and E3 genes and the proteins that these genes encode.

The E3 glycoprotein is a disulfide-linked dimer having an apparent molecular weight of 124K. The precursors to E3 are primarily a 59K glycoprotein monomer which undergoes rapid dimerization to produce a 118K dimer. The 118K glycoprotein dimer undergoes further glycosylation to produce the 124K E3 (Deregt, D. and Babiuk, n. supra).

The reading frame of the E2 gene is 4089 nucleotides long and encodes a polypeptide of 1363 amino acids. The E3 gene is immediately 5' of the E2 gene on the viral genome and contains an open reading frame of 1272 nucleotides and encodes a polypeptide of 424 amino acids. The E3 gene terminates 14 nucleotides upstream from the E2 polypeptide initiation codon. The nucleotide sequence and predicted amino acid sequences of E2 and E3 are shown in FIGS. 3 and 4, respectively.

The present invention provides, inter alia, a subunit antigen useful in producing BCV vaccines.

BCV polypeptides from E2 and/or E3 are the subunit antigens in the present invention. Polypeptide subunit antigens are generally at least about 5 amino acids in length so as to encode an epitope, but are preferably at least about 10–15 amino acids in length. Typically, the antigens are about 20 or more amino acids in length. It is believed that no critical upper limit to the subunit antigen length exists. Thus, the subunit antigen can comprise an entire viral protein sequence, or even a fusion protein comprising the sequences of two or more of the viral glycoproteins.

The subunit antigens of the present invention can be either native E2 or E3 glycoproteins, fragments thereof, or recombinant E2 or E3 polypeptides. The recombinant subunits can be partial glycoprotein sequences, full-length protein sequences, or even fusion proteins (e.g., having appropriate leader sequences for the recombinant host, or with an additional subunit antigen sequence for BCV or another pathogen). Although the subunit antigen has epitopes derived from glycoproteins, it need not be glycosylated.

The preferred subunit glycoproteins of the present invention contain full-length (or near full-length) sequences of E2 or E3. Alternatively, shorter sequences that are antigenic (i.e., encode one or more epitopes) can be used. The shorter sequence may encode a "neutralizing epitope," which is defined as an epitope capable of eliciting antibodies that neutralize virus infectivity in an in vitro assay. Preferably the peptide should encode a "protective epitope" that is capable of raising in the host an "immune response;" i.e., either an antibody- or a cell-mediated response that protects an immunized host from infection or ameliorates the course of disease.

The subunit antigens of the present invention, particularly when comprised of short oligopeptides, may be conjugated to a vaccine carrier. Vaccine carriers are well known in the art: for example, bovine serum albumin (BSA), human serum albumin (HSA) and keyhole limpet hemocyanin (KLH). A preferred carrier protein, rotavirus VP6, is disclosed in EPO Pub. No. 0259149, the disclosure of which is incorporated by reference herein.

The polypeptides encoding BCV epitopes of the present invention may also be incorporated within particle-forming viral polypeptides as a fusion protein, as described in U.S. Pat. No. 4,722,840 and EPO Pub. No. 174,759. Alternatively, the BCV subunit antigens of the present invention can be incorporated into a foreign virus (e.g., vaccinia or adenovirus) as is known in the art.

Also within the skill in the art is to formulate the subunit antigen(s), with or without carriers, into a vaccine composition comprising a pharmaceutically acceptable vehicle and, if desired, an adjuvant. These formulations are preferably adapted for intramuscular injection, since intravenous injection is not usually practical for large-scale inoculation of domestic animals. Vehicles useful for parenteral injection are usually nontoxic and nontherapeutic. Such vehicles include water, saline solution, Ringer's solution, dextrose solution, and Hanks' solution. Nonaqueous vehicles, such as fixed oils, sesame oil, ethyl oleate, or triglycerides may also be used. Suspensions containing viscosity-enhancing agents such as sodium carboxymethylcellulose, sorbitol, or dextran may also be used. In addition, the vehicle usually will contain additives, for example to enhance isotonicity and chemical stability. Useful buffers include phosphate buffer, bicarbonate buffer, and TRIS buffer. Preservatives can include thimerosal, m- or o-cresol, formalin, and benzyl alcohol. Standard formulations are generally liquid injectables or solids capable of being dissolved in solution or suspended in a suitable liquid before injection. In a nonliquid formulation, therefore, the vehicle may comprise dextrose, bovine serum albumin, preservatives, etc., to which sterile water or saline are added before administration.

Also known within the art are adjuvants useful in the vaccine formulations of the present invention. Selecting the appropriate adjuvant and determining its proper concentration in the vaccine composition(s) of the present invention is also within the skill of the art. Adjuvants may include Freund's, aluminum salts, [Al(OH)$_3$, AlPO$_4$, Al$_2$(SO$_4$)$_8$], Ca$_3$ (PO$_4$)$_2$, muramyl di- and tri-peptides, saponin, DDA, Pluronics, oil-in-water emulsions (containing, e.g., dextran sulphate or vitamin E) and water-in-oil emulsions (containing, e.g., polysorbate 80).

The vaccines may also be orally administered with the subunits in a suitable oral carrier. Oral formulations include such normally-employed excipients as, for example, pharmaceutical grades of mannitol, lactose, starch, magnesium stearate, sodium saccharin cellulose, magnesium carbonate, and the like. Oral vaccine compositions may be taken in the form of solutions, suspensions, tablets, pills, capsules, sustained release formulations, or powders, containing from about 10% to about 95% of the active ingredient, preferably about 25% to about 70%. An oral BCV vaccine may be preferable to raise mucosal immunity in combination with systemic immunity raised by intramuscular administration of the vaccine.

In addition, the vaccine may be formulated into a suppository. For suppositories, the vaccine composition will include traditional binders and carriers, such as polyalkaline glycols or triglycerides. Such suppositories may be formed from mixtures containing the active ingredient in the range of about 0.5% to about 10% (w/w), preferably about 1% to about 2%.

Protocols for administering to animals the vaccine composition(s) of the present invention are within the skill of the art in view of the present disclosure. Those skilled in the art will select a concentration of subunit antigen(s) in the vaccine composition in a dose effective to elicit an antibody and/or T-cell response to the antigenic fragment. Within wide limits, the dosage is not believed to be critical. Typically, the vaccine composition is administered in a manner which will deliver between about 1 to about 1,000 micrograms of the subunit antigen in a convenient volume of vehicle, e.g., about 1–10 cc. Preferably, the dosage in a single immunization will deliver from about 1 to about 500 micrograms of subunit antigen, more preferably about 5–10 to about 100–200 micrograms (e.g., 5–200 micrograms).

The timing of administration may also be important. For example, a primary inoculation preferably may be followed by subsequent booster inoculations. It may also be preferred, although optional, to administer a second, booster immunization to the animal several weeks to several months after the initial immunization. To insure sustained high levels of protection against disease, it may be helpful to readminister a booster immunization to the animals at regular intervals, for example once every several years. Alternatively, an initial dose may be administered orally followed by later inoculations, or vice versa. Preferred vaccination protocols can be established through routine vaccination protocol experiments.

The subunit antigen can be produced from protein recovered from virus or virus-infected cells. For example, purified virus or virus-infected cells can be disrupted or lysed and subjected to immunoadsorbent chromatography to purify E1 or E2. The production of monoclonal antibodies is within the skill of the art. Briefly, a mammal, such as a mouse, is immunized with either purified virus or the purified viral glyco protein of interest (e.g., SDS-PAGE purified) and antibody-producing B lymphocytes recovered. Typically, these B lymphocytes are then fused with a continuous cell line to produce an immortal antibody producing cell line; i.e., a hybridoma, trioma, etc. Immortal, antibody-producing cell lines can also be created by techniques other than fusion, such as direct transformation of B lymphocytes with oncogenic DNA, or transfection with Epstein-Barr virus. See, e.g., M. Schreier et al., *Hybridoma Techniques* (1980); Hammerling et al., *Monoclonal Antibodies and T-Cell Hybridomas* (1981); Kennett et al., *Monoclonal Antibodies* (1980); see also U.S. Pat. Nos. 4,341,761; 4,399,121; 4,427, 783; 4,444,887; 4,451,570; 4,466,917; 4,472,500; 4,491, 632; 4,493,890. Native BCV proteins which are immunopurified can be used in their entirety as subunit antigens, or fragments of the entire proteins containing the neutralizing epitopes can be employed as subunit antigens.

Non-native BCV polypeptides can be produced by a number of methods. For example, oligopeptides containing neutralizing epitopes can be prepared synthetically by known techniques. See, e.g., U.S. Pat. No. 4,735,896. It is preferred, however, to prepare the non-native polypeptide subunit antigens by recombinant DNA methods.

Recombinant polypeptide subunit antigens are produced according to the present invention by constructing an expression cassette and transforming a host cell therewith to provide a cell line or culture capable of expressing the subunit antigen which is encoded within the expression cassette. The first step in constructing the expression cassette is to obtain a coding sequence for the glycoprotein or glycoprotein epitopes of interest. Coding sequences for E2 and E3 are shown in FIGS. 3 and 4. Thus, coding sequences can either be prepared directly by synthetic methods based on the disclosed sequence (or equivalent sequences encoding the same amino acids), or by using the disclosed sequence to design oligonucleotide probes to clone coding sequence using known techniques. The coding sequence can be comprised entirely of BCV glycoprotein-encoding sequences, or such glycoprotein sequences can be fused to other sequence (e.g., leader sequences) so that a fusion protein is encoded. See, e.g., U.S. Pat. Nos. 4,431,739; 4,425,437; 4,338,397. Synthetic coding sequences will also allow for the convenient construction of coding sequences which express BCV glycoprotein analogs or "muteins." Alternatively, coding sequences for muteins can be prepared by site-directed mutagenesis of native BCV nucleotide sequences. The techniques of site-directed mutagenesis are known in the general art.

Once an appropriate coding sequence for the subunit antigen has been prepared or isolated, it can be cloned into any suitable vector or replicon. Numerous cloning vectors or replicons are known to those of skill in the general art, and the selection of an appropriate cloning vector is a matter of choice. Examples of recombinant DNA vectors for cloning and host cells which can be transformed include various bacteriophage lambda vectors (*E. coli*), pBR322 (*E. coli*), pACYC171 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillis subtilis*), pBD9 (Bacillis), pIJ61 (Streptomyces), pUC6 (Streptomyces), actinophage dC31 (Streptomyces), YIp5 (Saccharomyces), YCp19 (Saccharomyces), 2-micron plasmid (Saccharomyces), and bovine papilloma virus (mammalian cells). See, generally, *DNA Cloning*, vols. I & II, supra; Maniatis et al., supra; Perbal, supra.

To complete construction of expression cassettes, the coding sequence as described above for the subunit antigens is then operably linked to control sequences (e.g., a promoter, etc.), so that the DNA sequence encoding the subunit antigen is transcribed into messenger RNA in the host cell transformed by the expression cassette. In general, the coding sequence will be downstream from the promoter sequence and any expression regulatory regions, such as enhancers or operator sequence. If the subunit antigen coding sequence is linked to a heterologous coding sequence or start codon, then it is important to place the subunit antigen coding sequence in reading frame with the latter. If the intended expression host is procaryotic, then it will also be necessary to include a ribosome binding site among the upstream control sequences. Downstream operably linked control sequences will usually comprise a transcription termination sequence, and a polyadenylation signal (for mammalian expression hosts).

When the intended expression host is a procaryotic or yeast cell, the promoter and other control sequences will necessarily be heterologous to the subunit antigen coding sequence. If the selected expression host cell is a mammalian cell, the control sequences can be homologous BCV sequences, or preferably heterologous mammalian control sequences. The expression cassette can be constructed, for example, as a discrete molecular entity flanked by convenient restriction sites, or it can be constructed by inserting the coding sequence into a previously constructed expression vector with an appropriate insertion site.

A number of procaryotic expression vectors are known. See, e.g., U.S. Pat. Nos. 4,440,859; 4,436,815; 4,431,740; 4,431,739; 4,428,941; 4,425,437; 4,418,149; 4,411,994; 4,366,246; 4,342,832; see also U.K. Publication Nos. GB2,121,054; GB2,008,123; GB2,007,675; and European Publication No. 103,395. The preferred procaryotic expression vectors are those for *E. coli*. Other preferred expression vectors are those for use in eucaryotic systems. Yeast expression vectors are also known. See, e.g., U.S. Pat. Nos. 4,446,235; 4,443,539; 4,430,428; see also European Publication Nos. 103,409; 100,561; 96,491.

Preferred expression hosts of the present invention are mammalian cells. Various cell lines and expression vectors are known in the art. Examples of appropriate mammalian expression hosts include kidney cell lines (e.g., Madin Darby bovine kidney and CV-1 monkey kidney cell lines), fibroblast cell lines (e.g., human, murine or chicken embryo fibroblast cell lines), Chinese hamster ovary (CHO) cells, HeLa cells, mouse NIH/3T3 and/or $LMTK^-$ cells. It is also known to express heterologous proteins in myeloma cell lines employing immunoglobulin promoters. See, e.g., Banerji et al. (1983), *Cell* 33:729–740; U.S. Pat. No. 4,663,281. The selection of a mammalian cell line is not critical. Various mammalian expression vectors employing viral promoters (e.g., SV40 early region promoter, Rous sarcoma virus, LTR promoter, etc.) are also well known in the art. See, e.g., Gorman et al. (1982), *Proc. Natl. Acad. Sci. USA* 79:6777–6781; Southern et al. (1982), *J. Mol. App. Genet.* 1:327–341; PCT Publication No. W087/02062. Preferred eucaryotic expression vectors are those employing the vaccinia virus, the SV40 virus, or the Rous sarcoma virus. See, e.g., Mackerr et al. (1984), *J. Virol.* 49:857; *DNA Cloning, vol.* II, pp. 191–211, supra; PCT Publication No. W086/07593; Chakrabarty et al. (1985), *Mol. Cell. Biol.* 5:3403.

Another preferred embodiment of the present invention is the expression of recombinant BCV polypeptides in insect cells using viral vectors, such as baculovirus. For example, high levels of expression have been achieved with vectors based on *Autographa californica* nuclear polyhedrosis virus (AcNPV) in *Spodoptera frugiperda* cells. See, e.g., Smith et al. (1983), *J. Virol.* 46:584–593; EPO Pub. No. 0259149, supra.

Generally, a host cell which has been stably transformed by an expression cassette for the subunit antigen is selected to produce the recombinant poly peptide. A stably transformed host is one wherein the expression cassette has integrated into the host cell's chromosome. Alternatively, in the case of bacteria or yeast expression hosts, it may be preferred to select expression hosts that do not integrate the expression cassette but maintain the cassette on a nonintegrating episomal element, such as a plasmid. The subunit antigen is produced by growing host cells transformed by the expression cassette under conditions which cause the expression of biologically active subunit antigen polypeptide. The appropriate conditions to bring about expression are well known in the art, and will depend primarily on the expression system and host selected. The subunit antigen polypeptide may be isolated from the host cells and purified. If the expression system secretes the subunit antigen, then the polypeptide can be purified directly from the growth media. If subunit antigen is not secreted, however, it may be necessary to disrupt the host cells and purify the subunit antigen polypeptide from the cellular lysate. Various purification techniques, such as SDS-PAGE, HPLC and immunoaffinity chromatography, are known, and the selection of the appropriate purification and recovery method is within the skill of the art.

Described below are examples of the present invention. These examples are provided only for illustrative purposes and are not intended to limit the scope of the present invention in any way. In light of the present disclosure, numerous embodiments within the scope of the claims will be apparent to those of ordinary skill in the art. The contents of the references cited in the specification are incorporated by reference herein.

C. EXAMPLES

Example I

Molecular Cloning of the BCV Genome

The Quebec isolate of bovine coronavirus (Dea et al., (1980) *Amer. J. Vet. Res.* 41:30–38) was propagated in Madin-Darby bovine kidney (MDBK) cells and purified by polyethylene glycol precipitation and sucrose gradient centrifugation as described previously (Deregt et al., (1987) *J. Gen Virol.* 68:2863–2877). Genomic RNA was prepared by phenol:chloroform:isoamyl alcohol (50:48:2) extraction and ethanol precipitation. Oligo-dT primed synthesis of double-stranded cDNA was carried out by standard methods (Gubler et al., supra, and Maniatis et al., supra). After addition of BamHI linkers, the double-stranded cDNA was fractionated by electrophoresis on Tris-borate buffered 1% agarose gels and cDNA of greater than 3000 nucleotide bp pairs was ligated to BamHI-cleaved pTZ 19R multifunctional plasmid (Pharmacia). The ligation mix was used to transform *E. coli* strain DHI. Recombinant colonies were identified by in situ hybridization with radiolabeled cDNA prepared by random priming of reverse transcription of virion genomic RNA or random priming cDNA synthesis with the Klenow fragment of DNA polymerase I utilizing denatured restriction fragments as template.

Northern Blotting

Total cellular RNA was extracted from BCV-infected MDBK cells 18 hrs after infection. Infected cells were lysed in 20 mM tris-HCl, pH 8.0, 50 mM KCl, 5 mM MgCl$_2$ containing 1% NP-40 and 0.5% sodium deoxycholate. After brief vortexing and centrifugation at 12,000×g for 1 min, the supernatant was extracted with phenol:chloroform:isoamyl alcohol and ethanol precipitated. Poly A+ RNA was selected by oligo-DT cellulose chromatography (Aviv et al., (1972) *Proc. Natl. Acad. Sci.* 69:1408). RNA was electrophoresed on 1% formaldehyde-agarose gels (Lehrach et al., (1977) *Biochemistry* 16:4743–4748) and electroblotted onto Zeta-Probe membrane (Biorad). Radiolabeled probes were prepared as described above and hybridization was carried out following the manufacturer's directions.

DNA Sequencing cDNA clones representing the E2 and E3 genes of BCV in plasmid pTZ 19R were sequenced using the dideoxy chain termination method (Sanger et al., (1977) *Proc. Natl Acad. Sci.* 74:5463–5467) after generation of an extensive series of overlapping deletions (Henikoff et al., (1984) *Gene* 28:351–359).

In Vitro Transcription and Translation

Expression constructs of the BCV E2 gene were prepared by exonuclease III digestion to remove flanking cDNA sequences (Henikoff et al., supra). BCV E2 sequences extending from nucleotide 6 to 4129 and E3 sequences extending from nucleotide 10 through 1305 were subcloned into the BamHI site of pTZ 19R. After EcoRI digestion, m7GpppA-capped transcripts were synthesized with T7 RNA polymerase (Melton et al., (1984) *Nuc. Acids Res.* 12:7035–7056) and translated in rabbit reticulocyte extracts containing 600 uCi/ml 35S-methionine (Amersham, f800 Ci/mmole). The products were immunoprecipitated with pooled monoclonal antibodies described by Deregt et al., (1987) *Virology* 161:410–420, electrophoresed on 13% acrylamide:DATD (30:1.4) gels according to Laemmli (1970) *Nature* (London) 227: 680–685, and fluorographed.

Construction of E2 and E3 Clones and Expression in Insect Cells by Recombinants of *Autographa californica* baculovirus Because clones pCVA12H and pCVA12I contained partially overlapping segments of the E2 gene, a single clone containing the entire E2 gene was constructed by fusing the 5' BamHI-PstI fragment from pCVA12H to the 3' PstI-BamHI fragment of pCVA12I. Noncoding sequences were removed from the 5' end of the construct by exonuclease III digestion and addition of a BamHI linker. Noncoding sequences were removed from the 3' end of the gene by partial digestion with TaqI and addition of a BamHI linker. The resulting sequence is shown in FIG. 3.

The expression construct of E3 was constructed by exonuclease III treatment of the 3' end of pCVA12H to a point 51 nucleotides downstream from the initiation codon of the E2 gene. The 5' end of pCVA12H was digested with MboII, and BamHI linkers were added. Therefore, the final gene construct begins 9 nucleotides plus a BamHI linker (44 nucleotides) upstream of the E3 initiation codon and terminates 51 nucleotides into the E2 gene.

The gene constructs were then subcloned in baculovirus transfer vector pVL941 and inserted into the genome of *A. californica* baculovirus by homologous recombination. Recombinant viruses were identified by plaque hybridization and several rounds of plaque purification.

Monolayers of *Spodoptera frugiperda* cells (SF9) were infected with the recombinant baculoviruses and incubated at 28° C. At the times indicated, the medium was replaced with methionine-free Grace's medium containing 50 uCi/ml of $^{35}$S-methionine for 2 hours. The cells were collected and lysed in RIPA buffer. The radiolabeled products were immunoprecipitated with monoclonal antibody and analyzed by SDS-polyacrylamide gel.

Expression of BCV Genome

Expression constructs of the BCV E2 gene were prepared by exonuclease III digestion to remove flanking cDNA sequences (Heinkoff, Supra). BCV E2 sequences extending from nucleotide 6 to 4129 and E3 sequences extending from nucleotide 10 through 1305 were subcloned into the baculovirus transfer vectors PYMI and pVL941, respectively (Matsuura, Y., et al. (1987) *J. Gen. Virol.* 68:1233–1250, and Summers, M. D., and G. E. Smith (1987) Texas Agricultural Experiment Station Bulletin 1555). The genes were then inserted into the genome of the baculovirus *Autographa californica* by homologous recombination. Recombinant viruses were identified by plaque hybridization and serial plaque purification. *Spodoptera frugiperda* cells were infected with the plaque purified recombinant viruses and incubated at 28° C. for 36 hours. The media was removed and replaced with Grace's medium lacking methionine containing 50 uCi/ml $^{35}$S-methionine (Amersham, f800 Ci/mMole) and incubated an additional 2 hours. The cells were scraped into phosphate-buffered saline and pelleted at 1000×g for one minute and lysed in RIPA buffer containing 1% NP-40 and 1% sodium deoxycholate. Nuclei and insoluble material were removed by centrifugation at 15,000×g for 5 minutes and the recombinant polypeptides were immunoprecipitated with monoclonal antibodies. The precipitated products were analyzed by electrophoresis on 10% polyacrylamide gels (Laemmli, (1970) *Nature* (London) 227:680–685) and fluorography.

Characterization of the Polypeptide Products of the BCV E2 and E3 Genes

In order to demonstrate directly that the cloned sequences represented the genes for the BCV E2 and E3 genes, the sequences shown in FIGS. 3 and 4 were subcloned in the *Autographa californica* baculovirus and expressed in insect cells.

Expression of the BCV E3 gene in insect cells yielded a polypeptide of approximately 120K when analyzed in the absence of 2-mercaptoethanol. Addition of 2-mercaptoethanol to the immunoprecipitated product prior to electrophoresis dissociated the 120K product to a monomeric 56K polypeptide. The ability of E3-specific monoclonal antibodies to specifically precipitate the product and its electrophoretic mobility in the presence and absence of 2-mercaptoethanol demonstrate that the cloned sequence does represent the gene for the BCV E3 polypeptide.

Expression of the BCV E2 gene in insect cells and immunoprecipitation with E2-specific monoclonal antibodies yields a product of approximately 200K. A similar 200K polypeptide which represents the uncleaved form of the E2 polypeptide is also detected in BCV infected mammalian cell lines. Trypsin treatment of insect cells expressing the BCV E2 gene also results in cell fusion, a characteristic property of cells expressing the BCV E2 protein.

Results

Isolation of cDNA Sequences Representing the BCV E2 Gene

Figure 2:
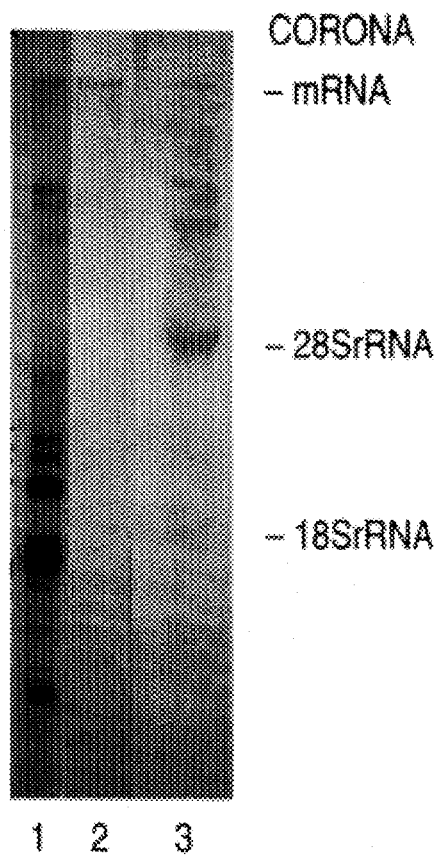
FIG. 2 shows a Northern blot analysis of BCV RNA.

Restriction mapping of cloned cDNA inserts initially resulted in a linear map representing approximately 4,000 nucleotides of the BCV genome, as shown for clone pCVA12 (FIG. 1). In order to determine the proximity of these sequences to the 3' end of the virion genome, electrophoretically resolved preparations of poly(A)+ RNA from BCV infected MDBK cells were probed with sequences from the 3' end of pCVA12 (solid box in FIG. 1). Since coronavirus mRNAs form a 3' nested set (Sterns and Kennedy, 1980), a probe homologous to the 3' end of the viral genome hybridizes to all of the viral mRNAs detected with a probe representative of the entire genome. To produce the Northern blot in FIG. 2, total intracellular RNA was extracted from BCV-infected MDBK cells 18 hours postinfection. Viral genome RNA was extracted from purified virus. RNA was electrophoresed on 1% formaldehyde-agarose gels and electroblotted onto Zeta Probe membrane. Hybridization was in 50% formamide, 5×SSC at 42° C. Lanes 1, 3, BCV-infected MDBK intracellular RNA; lane 3, viral genomic RNA. Probes: lanes 1 and 2, 3' portion of pCVA12 indicated in FIG. 1; lane 3, clone pCVA12H. As shown in FIG. 2, lane 1, radiolabeled cDNA representing the 3' end of clone pCVA12 hybridized to 8 species of intracellular RNA, numbered mRNA 1 through 8, which have been detected with cDNA probe representative of the entire viral genome. The origin of the numerous small RNA species is unknown but might represent intermediates of transcription or replication as described in MHV-infected cells (Baric et al., (1987) Virology 156:342–354). RNA 1, which may direct the synthesis of nonstructural polypeptides, corresponds to the viral genome RNA (FIG. 2, lane 2). RNAs 5 through 8 direct the synthesis of 14K NS, 10K NS, matrix (E1) and the nucleocapsid protein (N) respectively (Lapps et al., (1987) Virology 157:47–57). Additional restriction mapping of pCVA12 and comparison with the sequences at the 3' end of the viral genome recently reported (Lapps et al. supra), showed that clone pCVA12 represents sequences at or very near the 3' end of the genome and extends approximately 4000 nucleotides upstream (FIG. 1).

Based upon the molecular weight of the BCV E2 precursor of approximately 190K (Deregt et al., supra), it was predicted that RNA 4 was the only mRNA likely to contain sufficient unique sequences to encode the BCV E2 polypeptide. In order to identify clones which hybridize only to mRNA 1–4 and may thereby represent the E2 gene, approximately 25,000 colonies were probed with the 5' end of clone pCVA12 (cross hatched in FIG. 1). As shown in FIG. 2, lane 3, a series of clones, represented by pCVA12H hybridized only to mRNA 1 through 4. Sequencing of the cDNA insert from pCVA12H and the overlapping 5' portion of pCVA12I identified a single open reading frame of 4089 nucleotides. Based upon a comparison to the sequence of the E2 gene of MHV-JHM (Schmidt et al., (1987) J. Gen. virol. 68:47–56) and hydropathic analysis (Kyte et al., (1982) J. Mol. Biol. 157:105–132) of the predicted gene product, the nucleotide sequence shown in FIG. 3 represents the complete sequence of the BCV E2 gene.

The sequence shown in FIG. 3 extends 14 nucleotides upstream from the E2 initiation codon and abuts the termination codon for another upstream open reading frame (see below). Immediately preceding the ATG of E2 is the conserved heptanucleotide sequence TCTAAAC similar to the intergenic regions upstream of the BCV M and N genes except that the conserved sequences begin 10 and 14 nucleotides upstream of the M and N genes, respectively (Lapps et al., supra).

The predicted polypeptide product of the BCV E2 gene is 1363 amino acids long and has a molecular weight of 150K exclusive of glycosylation. There are 21 potential N-linked glycosylation sites, 11 in the proposed S1 subunit and 10 in the S2 subunit, however, it is not known how many of these sites are glycosylated.

Immediately following the initiation codon, an extremely hydrophobic stretch of 15 amino acids may function as the signal sequence to direct transport of the nascent E2 polypeptide across the membrane of the rough endoplasmic reticulum. Another region of extreme hydrophobicity is near the carboxy terminus of S2, which may serve to anchor the S1/S2 dimer of the large peplomer into the virion envelope.

Characterization of the E3 Gene

Bovine coronavirus contains a second surface glycoprotein, E3, which is unique to mammalian coronaviruses which exhibit hemagglutinating activity. Based upon a molecular weight of 59K for the mature polypeptide (Deregt et al., supra), inspection of the Northern blot in FIG. 2, lane 1, there are 3 mRNA in coronavirus-infected cells to which a polypeptide product have not been assigned. RNA 1 in FIG. 1 is identical to the virion genome and appears to have unique sequence in great excess of that necessary to encode the E3 polypeptide assuming that E3 is not derived by cleavage of a higher molecular weight precursor. No such precursor has been reported. RNAs 2 and 3 appeared to have adequate unique sequence such that either of these two RNAs could direct the synthesis of E3. The nested nature of coronavirus mRNA suggested that the sequences unique to mRNA 3 were present immediately 5' to the gene for E2 in clone pCVA12H. The sequence of the 1500 nucleotides at the 5' end of pCVA12H was determined and found to contain an open reading frame of 1272 nucleotides terminating 14 nucleotides upstream of the E2 initiation codon and encoding a polypeptide of 424 amino acids (FIG. 4). As shown for the other genes of BCV, the gene is also preceded by the characteristic heptanucleotide ACTAAAC, beginning 16 nucleotides upstream from the probable initiation codon.

Hydrophobicity analysis of the predicted polypeptide product of the unique sequences of mRNA 3 indicated that the polypeptide has the characteristics of a membrane glycoprotein. Immediately following the initiation codon is a stretch of 15 hydrophobic amino acids which may be the signal for translocation of the glycoprotein across the membranes of the rough endoplasmic reticulum. Comparison of this amino acid sequence with the predicted amino terminal sequence of E2 shows that 5 of the first 6 amino acids are identical. Previous experiments have shown that the E3 of BCV is glycosylated by a tunicamycin-sensitive mechanism (Deregt et al., supra) and the predicted polypeptide has 9 possible sites for the addition of N-linked oligo-saccharides. The carboxy terminus of the polypeptide also has an extremely hydrophobic sequence which may serve to anchor the polypeptide in the virion envelope.

Characterization of the Polypeptide Products Produced from the Cloned BCV E2 and E3 Genes

Plasmid

In order to demonstrate directly that the cloned E2 sequence and the gene immediately adjacent 5' to the E2 gene are the genes for the peplomer and E3 polypeptides, respectively, the sequences shown in FIGS. 3 and 4 were subcloned into plasmid pTZ 19R and transcribed in vitro. To produce the results shown by the SDS-PAGE gel in FIG. 5, BCV E2 and E3 cDNA clones were transcribed in vitro and translated in rabbit reticulocyte lysates. After immunoprecipitation with monoclonal antibodies, the products were analyzed by SDS-polyacrylamide gel electrophoresis on 13% acrylamide:DATD gels.

Figure 5:
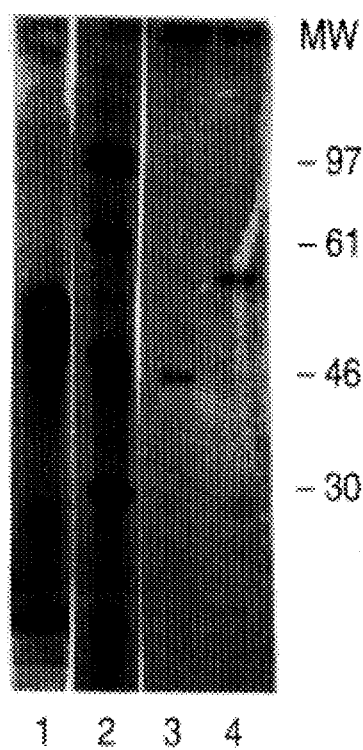
FIG. 5 is a photograph of an SDS-PAGE gel on which proteins produced by in vitro translation of mRNA produced from BCV E2 and E3 genes subcloned into plasmid (pTZ 19R) are analyzed. Below the photograph are lane numbers, to the right hand side of the photograph are numbers indicating molecular weights. Lane 1, E2 gene product; lane 2, molecular weight markers; lane 3, E3 gene products; lane 4, E3 gene products synthesized in the presence of pancreatic microsomes. MW, molecular weights$\times 10^{-3}$.

In vitro translation of the E2 gene transcripts yielded four polypeptides of 29K, 44K, 50K and 55K which were immunoprecipitated with E2 specific monoclonal antibodies (FIG. 5, lane 1). The products are similar to those obtained by in vitro translation of poly A+ mRNA from BCV-infected cells (not shown), indicating that the low molecular weights are probably due to the difficulty in translating the large E2 mRNA in vitro.

In vitro translation of transcripts of the cloned E3 gene and immunoprecipitation with E3 specific monoclonal antibodies yields a polypeptide of 45K (FIG. 5, lane 3), as predicted based upon the nucleotide sequence of the cDNA clone shown in FIG. 4.

Baculovirus

In order to demonstrate directly that the cloned sequences represented the genes for the BCV E2 and E3 polypeptides, the sequences shown in FIGS. 3 and 4 were also subcloned into the A. californica baculovirus genome and expressed in insect cells.

Figure 6:
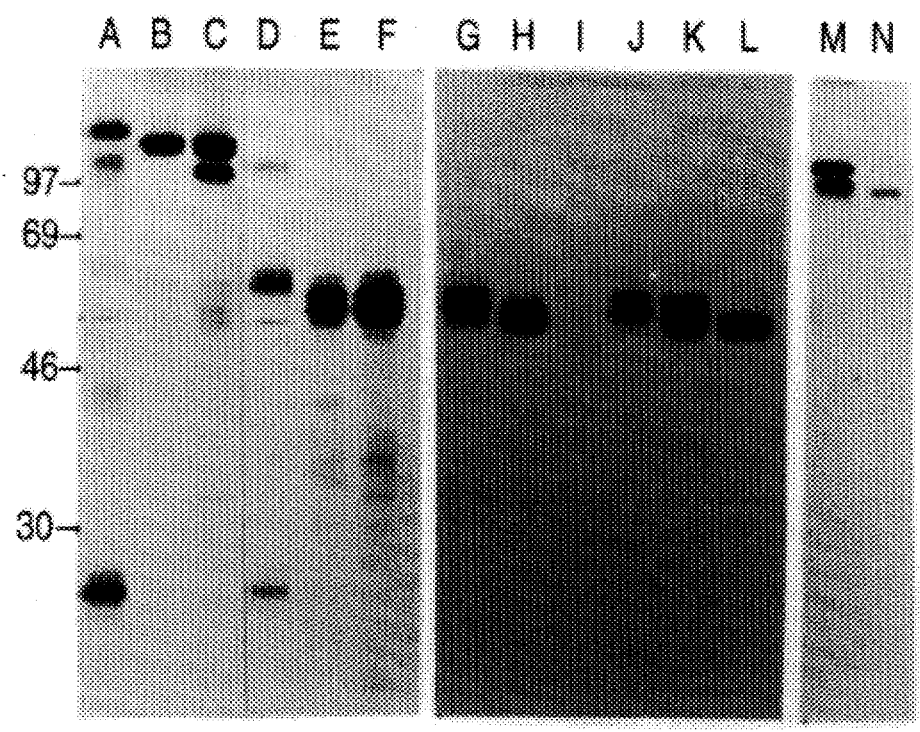
FIG. 6 is a photograph of a PAGE gel which shows expression of the BCV E3 polypeptide in AcNPV-infected insect cells. Lanes are indicated across the top by capital letters; molecular weights ($\times 10^{-3}$) are vertical along the lefthand side of the figure.

To produce the result shown in FIG. 6, recombinant AcNPV-infected cells were radiolabeled as indicated and immunoprecipitated with E3-specific monoclonal antibodies prior to electrophoresis on 10% SDS-polyacrylamide gels. Lanes A-C show unreduced forms of E3 produced in BCV-infected MDBK cells, BLVE3-infected Sf9 cells, and BAE3S-infected Sf9 cells, respectively. Lanes D–F show forms as in A–C after reduction with 2-mercaptoethanol. FIG. 6 also shows pulse-chase analysis of Sf9 cells producing recombinant E3 polypeptide. Lane G shows E3 polypeptides after 2-hour label. Lane H shows cell-associated BVLE3 products after 12-hour chase. Lane I shows immunoprecipitation of media from BVLE3-infected cells after 12-hour chase. Lane J shows cell-associated products of BAE3S-infected Sf9 cells after 2-hour label. Lane K shows cell-associated products of BAE3S-infected Sf9 cells after 12-hour chase. Lane L shows immunoprecipitation of media from BAE3S-infected Sf9 cells after 12-hour chase. Lanes M and N show dimeric forms from BAE3S-infected cells and media, respectively, after 12-hour chase.

Figure 7:
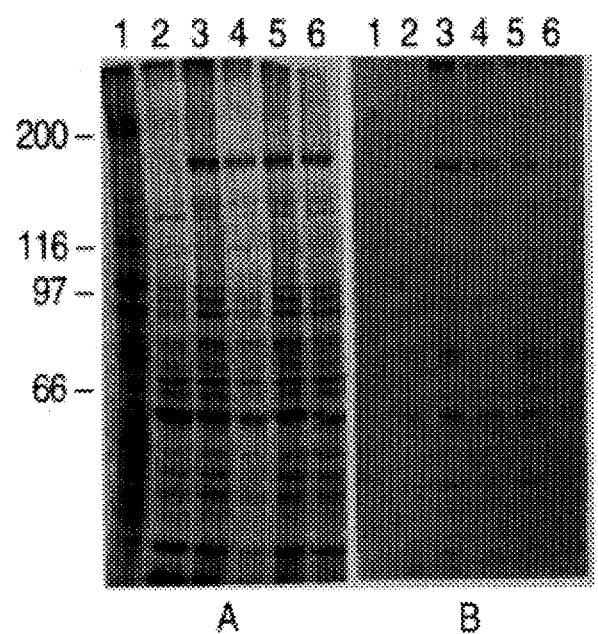
FIG. 7 is a photograph of a PAGE gel which shows synthesis of the BCV E2 polypeptide by recombinant baculovirus in S. frugiperda cells. Lanes are indicated across the top by numbers; panels are indicated below by capital letters. Molecular weights ($\times^{-3}$) are indicated at the left of the figure.

To produce the results shown in FIG. 7, cells were infected with baculovirus recombinants at a multiplicity of 5. At 40 hours post-infection, the cells were radiolabeled for one hour with 100 uCi/ml 35S-methionine. The cells were harvested and lysed in RIPA buffer, and total cell extracts were analyzed by electrophoresis on 7.5% polyacrylamide gels. Panel A presents an analysis of whole cell lysates. Lane 1, shows uninfected cells. Lane 2, shows A. californica-infected cells. Lanes 3–6 show cells infected with recombinants AcE2A, -B, -C, and -D, respectively. Panel B presents immunoprecipitated products, as in Panel A. Arrows indicate the positions of the 180 kDa E2 and 145 kDa $E2_c$ (c=core, or unglycosylated) polypeptides.

Expression of the BCV E3 gene in insect cells yielded a polypeptide of approximately 56K which is immunoprecipitated with E3-specific monoclonal antibodies, as shown in FIG. 6. The polypeptide migrates slightly more rapidly than the authentic protein from purified BCV virions. The ability of monoclonal antibodies to specifically immunoprecipitate the polypeptide proves the identity of the polypeptide and indicates that the recombinant protein is immunologically identical to the native viral polypeptide.

Expression of the E2 polypeptide in insect cells, as shown in FIG. 7, yields two polypeptides of approximately 180K and 145K which are immunoprecipitated by monoclonal antibodies specific for the E2 polypeptide of bovine coronavirus. Tunicamycin treatment of the insect cells results in a decrease of the 180K product with an increase in the 145K product which demonstrates that the 145K polypeptide is a nonglycosylated form of the E2 polypeptide.

At the amino acid sequence level, there is some similarity between murine hepatitis virus strains JHM, A59, and bovine coronavirus E2 glycoproteins (Schmidt et al. (1987); de Groot et al. (1987); our unpublished data). The amino acid sequences of the bovine coronavirus and murine hepatitis virus E2 glycoproteins and our calculations on the degree of homology as shown in FIG. 8. Sequences are aligned to show maximum homology. Upper case letter indicates a conserved residue at that specific position. Each hyphen "-" means a gap of one residue has been introduced in order to maximize homology. In each case, the BCV sequence is the top line. Amino acid numbers at the beginning of each line are noted at the left margin. In the plot shown, conservative changes are considered as nonhomologous. At this stringency, MHV-JHM is 69.1% homologous to BCV and A59 is 67.7%. At a lower stringency in which the following substitutions are considered conservative, S=T, K=R, F=L=M=I=V, H=Y=W, A=C, the homologies increase to 75.5 and 73.9%, respectively.

These values completely ignore the fact that BCV contains additional sequence which is not represented in the other two viruses. If the additional sequence in BCV is considered in the comparison, the values decrease to 62.7 and 67.7% under a high stringency comparison and 68.4 and 71.8% under conditions in which the conservative substitutions are considered as homologous.

Example II

Analysis of the S Spike (Peplomer) Glycoprotein of Bovine Coronavirus Synthesized in Insect Cells Briefly, in this Example, the bovine coronavirus (BCV) spike glycoprotein precursor (S, formerly termed peplomer or "E2") and its two subunit polypeptides (S1 and S2) were individually expressed in Spodoptera frugiperda (Sf9) insect cells. Each recombinant baculovirus expressed both glycosylated (S, formerly called "E2,"170K; S1, 95K; S2, 80K) and unglycosylated ($S_0$, 140K; $S1_0$, 75K; and $S2_0$, 65K) forms of BCV spike polypeptides in Sf9 cells. The mature 95K S1 polypeptide was secreted whereas the S and S2 polypeptides remained cell-associated. The S precursor was partially cleaved in Sf9 cells, and the resulting S1 was also released into the medium. Neutralizing monoclonal antibodies representing two antigenic domains bound to recombinant S and S1 but not the S2 polypeptides, indicating that two major epitopes for BCV neutralization are located on the S1 subunit. (Yoo, et al., Virology 179:121–128 (1990), incorporated herein by reference.) Two nonoverlapping groups of monoclonal antibodies (A and B) have been identified which interact with the BCV S glycoprotein (Deregt, D. and Babiuk, L. A., Virology 68:410–420 (1987)). These monoclonal antibodies neutralize BCV infectivity in vivo (Deregt et al., J. Gen. Virol 70:993–998 (1989)) and in vitro (Deregt, D. and Babiuk, L. A., supra). However, the location of the neutralizing epitopes on the BCV S. glycoprotein have not yet been determined.

Recently, the baculovirus Autographa californica (AcMNPV) has been widely used as a helper-independent expression vector for high level foreign gene expression. Recombinant proteins appear to undergo proper post-translational modification and transport in insect cells (Luckow, V. A., and Summers, M. D., Bio/Technology 6:47–55 (1988); Miller, L. K., Annu. Rev. Microbiol. 42:177–199 (1988); and Cameron, I. R., et al., Trends Biotechnol. 7:66–70 (1989)). The peplomeric glycoprotein gene of BCV was introduced into the baculovirus genome to characterize the recombinant BCV peplomeric polypeptides produced in Sf9 cells, and demonstrate that the major neutralizing epitopes are located on the S1 subunit.

Materials and Methods

Cells and Viruses

S. frugiperda cells (Sf9, ATCC CRL 1711) were grown in suspension in TNM-FH medium containing 50 μg/ml of gentamycin supplemented with 10% fetal bovine serum (GIBCO) at 28° C. (Summers, M. D., and Smith, G. E., *Tex. Agric. Exp. Stn.* (*Bull.*) 1555 (1987)). The E2 strain of *A. californica* (AcMNPV) and the recombinant baculoviruses were propagated and titrated on a monolayer of Sf9 cells.

Cloning of Recombinant Plasmids

Restriction enzymes and DNA modifying enzymes were purchased from Pharmacia. FIG. 9 illustrates the primary structure of the recombinant spike proteins of BCV. The cloned S gene of BCV (Quebec strain) was obtained from plasmid pCVE2 (Parker, M. D. et al., *J. Gen. Virol.* 71:263–270 (1990)). For cloning of the S1-coding sequence, pCVE2 was digested with Tth111 I, which cleaved nucleotides 2294–2295 within the sequences encoding a putative proteolytic cleavage site of the S protein precursor, and asymmetric ends were blunted by Klenow fill-in reaction followed by digestion with BamHI. The 2.3-kb fragment was purified and ligated into the BamHI and blunt-ended XbaI sites of the pTZ18R. A universal translation termination sequence (5'GCTTAATTAATTAAGC-3') was subsequently inserted at the HincII site of the polylinker region and the resulting plasmid was termed pCVS1. pCVS1 was digested with SphI and repaired with $T_4$ DNA polymerase. A BamHI linker was then attached to the blunted SphI end followed by subsequent BamHI digestion and ligation into the BamHI site of the baculovirus transfer vector pAcYM1 (Matsuura, Y., et al., *J. Gen. Virol.* 68:1233–1250 (1987); a gift from Dr. C. Y. Kang, University of Ottawa, Canada). Briefly, to construct the S2 gene, a SphI-StyI fragment of pCVE2 (Parker, M. D. et al., *J. Gen. Virol.* 70:155–164 (1989)) was fused to a ScaI-SphI fragment from pCVE2 so that the resulting clone contained the entire S2-coding sequence proceeded by the sequence encoding 16 amino acids of the HE membrane translocational signal.

Antisera

Anti-BCV polyclonal rabbit sera and the BCV S-specific monoclonal antibodies were used as mouse ascitic fluids. Production and properties of the S-specific monoclonal antibodies, BB7-14, HF8-8, JB5-6, and HE7-3, have been previously described (Deregt, D. and Babiuk, L. A., supra).

Construction of Recombinant Viruses

A monolayer of *S. frugiperda* cells ($1.2\times10^6$ cells per 35-mm dish) was transfected with a mixture of 1 μg of AcMNPV genomic DNa and 2–4 μg of plasmid DNA in 20 mM Hepes, pH 7.05, 1 mM $Na_2HPO_4$, 5 mM KCl, 150 mM NaCl, and 100 mM glucose. Prior to inoculation, the above mixture was precipitated by incubation with $CaCl_2$ (final concentration 125 mM) at room temperature for 30 min. The transfection mix was removed after 1 hr and the cells were then further incubated with 2 ml of fresh medium. The supernatant was harvested after 4 days, and recombinant viruses were screened by plaque hybridization followed by several rounds of plaque purification (Summers, M. D. and Smith, G. E., supra). Construction of the recombinant baculoviruses containing the S precursor and S2 subunit genes (termed vAcS and vAcS2, respectively) are described in detail in Parker, M. D., et al., *J. Gen. Virol.* 71:263–270, and by Yoo, D., et al., *Virol.* 180:395–399 (1991).

Infection and Protein Analysis

Sf9 cells, at a density of $2\times10^6$ cells per 35-mm dish, were infected with baculoviruses at a m.o.i. of 10 to 20. The inoculum was removed after 1 hr adsorption and replaced with TNM-FH for further incubation. For in vivo radiolabeling, the medium was replaced with methionine-free Grace's medium for 1 hr. A total of 120 μCi/ml of [$^{35}$S]methionine (800 Ci/mmol, Amersham) was added and the cells were incubated for 4 hr. For pulse-chase studies, the cells were radiolabeled for 30 min, followed by addition of methionine-enriched TNM-FH for the indicated chase times. The cells were then washed with cold phosphate-buffered solution and lysed with 200 μl of RIPA buffer (1% Triton X-100, 1% sodium deoxycholate, 150 mM NaCl, 50 mM Tris-HCl, pH 7.4, 10 mM EDTA, 0.1% SDS). For the radioimmunoprecipitation, 1 μl of the appropriate antibody was incubated with a suspension of 10 mg protein A-Sepharose CL-4B beads (Pharmacia). The beads were washed three times with RIPA buffer and 20 μl of cell lysate was added to the beads for further incubation. The immune complexes were dissociated with sample buffer (10% SDS, 25% glycerol, 10% 2-mercaptoethanol, 10 mM Tris-HCl, pH 6.8, 0.02% bromophenol blue) and subjected to electrophoresis on a 7.5% discontinuous SDS-polyacrylamide gel followed by autoradiography.

Results

Synthesis of the S, S1 and S2 Polypeptides in Sf9 Cells

The synthesis of the BCV S polypeptides in insect cells infected with recombinant baculoviruses was measured by immunoprecipitation at 24 and 48 hr postinfection from the cells infected with vAcS, vAcS1, and vAcS2 recombinants, respectively. The 170K polypeptide in vAcS-infected cells was similar in migration rate to the uncleaved S precursor protein found in BCV-infected MDBK cells (Deregt, D. et al., *J. Gen. Virol.* 68:2863–2877 (1987)). The 95K and 80K polypeptides from the cells infected with vAcS1 and vAcS2 represented the S1 and S2 polypeptides, respectively. The recombinant S1 and S2 polypeptides were smaller in molecular weight than those of native corona virus (100K and 95K).

When the vAcS-infected cell lysate was analyzed 48 hr postinfection (see Yoo et al. (1990), supra, at FIG. 2B), in addition to the 170K polypeptide a 140K polypeptide ($S_0$) was immunoprecipitated (lane 8). Cells infected with vAcS1 and vAcS2 also produced two forms of recombinant polypeptides at 48 hr postinfection (see Yoo et al. (1990), supra, at FIG. 2B, lanes 9 and 10); the 95K (S1) and 75K ($S1_0$) polypeptides and the 80K (S2) and 65K ($S2_0$) polypeptides, respectively.

In order to determine if the 140K, 75K and 65K bands represented nonglycosylated forms of the corresponding mature polypeptide, tunicamycin treatment was carried out.

Tunicamycin, an inhibitor of N-linked glycosylation has been demonstrated to be effective in insect cells (Charlton, C. A. and Volkman, L. E., Virology 154:214–218 (1986)). The vAcS-infected cells were radiolabeled at 24 postinfection in the presence of various concentrations of tunicamycin. Only the 170K polypeptide is synthesized at this time of infection in the absence of tunicamycin (as shown in Yoo et al. (1990), supra, at FIG. 3A, lane 3). Tunicamycin at 15 µg/ml inhibited the production of the 170K polypeptide and only the 140K polypeptide was detected (Yoo et al. (1990), supra, at FIG. 3B, lane 4). This result suggested that the 140K polypeptide was the nonglycosylated immature form of the mature 170K S polypeptide. Similar results were obtained with vAcS1 (Yoo et al. (1990), supra, at FIG. 3C, lane 3) and vAcS2 (Yoo et al. (1990), supra, at FIG. 3D, lane 6), demonstrating that the 75K and 65K polypeptides were the nonglycosylated S1 and S2 polypeptides, respectively. Molecular weights of the nongylcosylated S, S1 and S2 polypeptides are consistent with those of predicted polypeptides deduced from the nucleotide sequences (Parker, M. D., et al., J. Gen. Virol. 71:263–270 (1990)). Cleavage of the S glycoprotein precursor in vAcS-infected cells was not detected either in the absence or presence of tunicamycin.

Neutralizing Epitopes of the S1 Subunit

Two antigenic domains responsible for BCV neutralization have been identified on the BCV S protein (Deregt, D. and Babiuk, L. A., supra). In order to approximate the location of these domains, the cell lysates prepared with vAcS1 or vAcS2 were reacted with monoclonal antibodies specific for each domain. The S (FIG. 10A) and S1 (FIG. 10C) polypeptides were immunoprecipitated by both group A, HE7-3 (lane 1), JB5-6 (lane 2), and HF8-8 (lane 3), and group B, BB7-14 (lane 4), monoclonal antibodies. None of monoclonal antibodies precipitated the S2 polypeptide (FIG. 10B, lanes 1–4) whereas the polyclonal antibody did (FIG. 10B, lane 5). These results indicate that two major neutralizing epitopes of BCV are located on the S1 subunit. The unglycosylated S and S1 polypeptides were also bound by these monoclonal antibodies (FIGS. 10A and 10C), suggesting that monoclonal antibodies HE7-3, JB-5-6, HF8-8, and BB7-14 were all glycosylation-independent. Furthermore, these results also indicate that the recombinant S and S1 polypeptides produced in Sf9 cells assume the proper conformation in the vicinity of these epitopes, since these monoclonal antibodies have been shown to recognize conformation-dependent epitopes (Deregt, D. and Babiuk, L. A., supra).

Secretion of the S1 Subunit and Partial Cleavage of the S Polypeptide

Since the S1 subunit has been found to contain major BCV neutralizing epitopes and because the sequences encoding the S1 subunit have been constructed to retain a membrane translocation signal, but not a membrane anchor, we showed the cellular transport of the S1 polypeptide in insect cells. In order to determine if the S1 polypeptide was secreted, cell culture supernatants were immunoprecipitated with S1-specific monoclonal antibodies and analyzed by SDS-PAGE. Cell labeling was done early in the infection period (20 hr p.i.) prior to the appearance of cytopathology. As shown in Yoo et al. (1990), supra, at FIG. 5, a 90K polypeptide was released into the culture medium (Id. at lanes 3 and 5) and had a slightly faster migration rate than the 95K intracellular counterpart (Id. at lanes 8 and 10). The decrease in the size of the 90K polypeptide was probably due to the further processing of the S1 polypeptide during the extracellular transport. When the culture medium from cells infected with vAcS was examined, the uncleaved S precursor polypeptide was not detected (Id. at lane 2), confirming that the presence of the S1 in the culture medium was not due to cell destruction. Previously, the recombinant S polypeptide was shown to be associated with the plasma membrane of Sf9 cells, (Parker et al. J. Gen. Virol. 71:263–270 (1990)). In addition, the S1-specific antibodies also precipitated a 90K polypeptide from the media of vAcS-infected cells (Id. at lane 2). This observation indicates that the S precursor is partially cleaved in Sf9 cells and the resulting S1 subunit is released to the medium. Taken together, all of these findings indicate that the signal sequence of the BCV S polypeptide is efficiently recognized in insect cells, and the S1 polypeptide is post-translationally processed and transported through the secretory pathway. Since the cells were labeled at an early stage of infection, neither the nonglycosylated S nor S1 were detected in the cells.

Discussion

Figure 9:
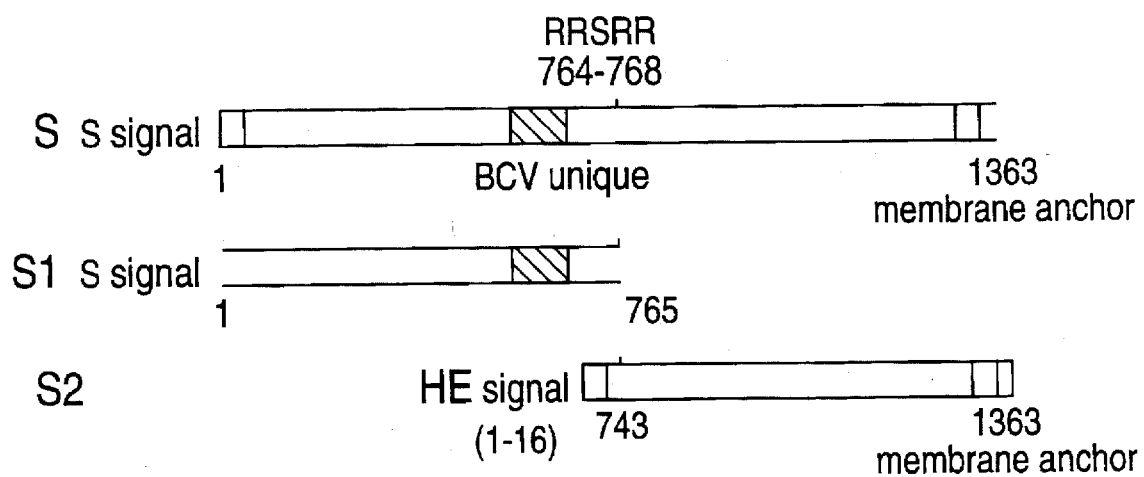
FIG. 9 is a diagram or schematic representation of primary structure of the recombinant spike polypeptides of BCV. For construction of the S1-coding sequence, the S sequence was cleaved within the sequence encoding a putative proteolytic cleavage site, and a translation termination sequence was attached. The S2-coding sequence was fused with the 5' terminal sequence of the BCV HE glycoprotein gene to contain a 16 amino acid HE membrane translocational signal. RRSRR indicates a putative proteolytic cleavage site. Shaded areas indicate hydrophobic domains. Numbers indicate amino acid positions. BCV unique region is regarded as an additional sequence when compared to that of the MHV-JHM S protein.

The S peplomeric precursor of BCV and its two subunit glycoproteins were expressed in Sf9 cells using a recombinant baculovirus vector. The S1 subunit coding sequence contained the entire upstream sequence, including the membrane translocation signal, from the putative cleavage site of the S precursor. Since the S2 coding sequence includes a membrane anchor but lacks a membrane translocational signal, the BCV HE signal sequence was attached to the N-terminus of the S2 gene (FIG. 9). All of the recombinant S, S1, and S2 polypeptides were glycosylated and immunoreactive with anti-BCV polyclonal antisera. Nonglycosylated forms were also detected at 36 hr. postinfection. The lack of glycosylation at later stages of baculovirus infection may be due to the saturation of the surface of rough endoplasmic reticulum by polyribosomes, the depletion of the N-glycosyl transferase, and/or other effects of baculovirus infection.

Molecular weights of the recombinant S1 and S2 polypeptides were estimated to be 95K and 80K, respectively, while the polypeptides produced in BCV-infected mammalian cells generally comigrate as 100K–110K (King et al., J. Virol 42:700–707 (1982), Deregt et al., Virol. 161:410–420 (1987). It seems likely that the molecular weight differences of the authentic versus recombinant S1 and S2 are due to the differences in the nature of glycosylation.

Secretion of the S1 polypeptide confirmed that the signal sequences of BCV S and BCV HE (formerly called "E3") glycoproteins were efficiently recognized in Sf9 cells, and directed membrane translocation and subsequent cellular transport. The recombinant S1 polypeptide was secreted into the culture medium from the cells, while the S precursor and the S2 subunit remained associated with the plasma membrane (Parker et al., J. Gen. Virol. 71:263–270 (1990). Even though both glycosylated and unglycosylated S1 polypeptides were present in the cells, only the glycosylated form was secreted (see Yoo et al. (1990), supra, at FIG. 6).

The extracellular form of the S1 polypeptide was slightly smaller by approximately 5K than the intracellular counterpart, as previously noted with a secreted form of the BCV HE polypeptide (Parker et al. J. Virol. 64:1625–1629 (1990)). It remains to be determined whether the difference in the size of the two forms are related to the primary structure of the polypeptide (i.e., cleavage of the signal peptide) or further modification of the oligosaccharides during or after the extracellular transport.

Cleavage of the BCV S precursor in Sf9 cells did not occur to a significant extent. Although the S1 polypeptide was detected in the vAcS-infected cell culture medium, the predominant form was the uncleaved S precursor. We were unable to detect the S2 portion of the cleaved S precursor, probably due to the limited amounts of cleaved products and the lack of monoclonal antibodies specific for the S2 subunit. However, cell fusion was observed in the vAcS-infected Sf9 cells, confirming the cleavage of the S precursor and the presence of the S2 subunit as a cleaved product (Yoo et al., manuscript in preparation). It is noteworthy that the cleavage of the recombinant S has not been previously observed in either IBV peplomer expression in vaccinia virus (Tomley et al., *J. Gen. Virol.* 68:2291–2298 (1987)) or MHV-JHM peplomer expression in baculovirus (Yoden et al., *Virology* 173:615–623 (1989).

Cleavage of the S peplomer appears to be important in coronavirus pathogenesis. Cell fusion is activated by proteolytic cleavage of the S protein (Sturman et al., *J. Virol.* 56:904–911 (1985); Yoo et al., *Virol.* (1991), supra). In MHV and IBV, it has been demonstrated that the S protein is responsible for the host-cell binding (Collins et al., *Virology* 119:358–371 (1982); Cavanagh et al., *J. Gen Virol.* 67:1443–1448 (1986)). While it is not clear whether the S protein of BCV also plays a role for the cell binding, it will be of interest to determine if proteolytic cleavage is related to the cell binding activity of the S protein.

Figure 10:
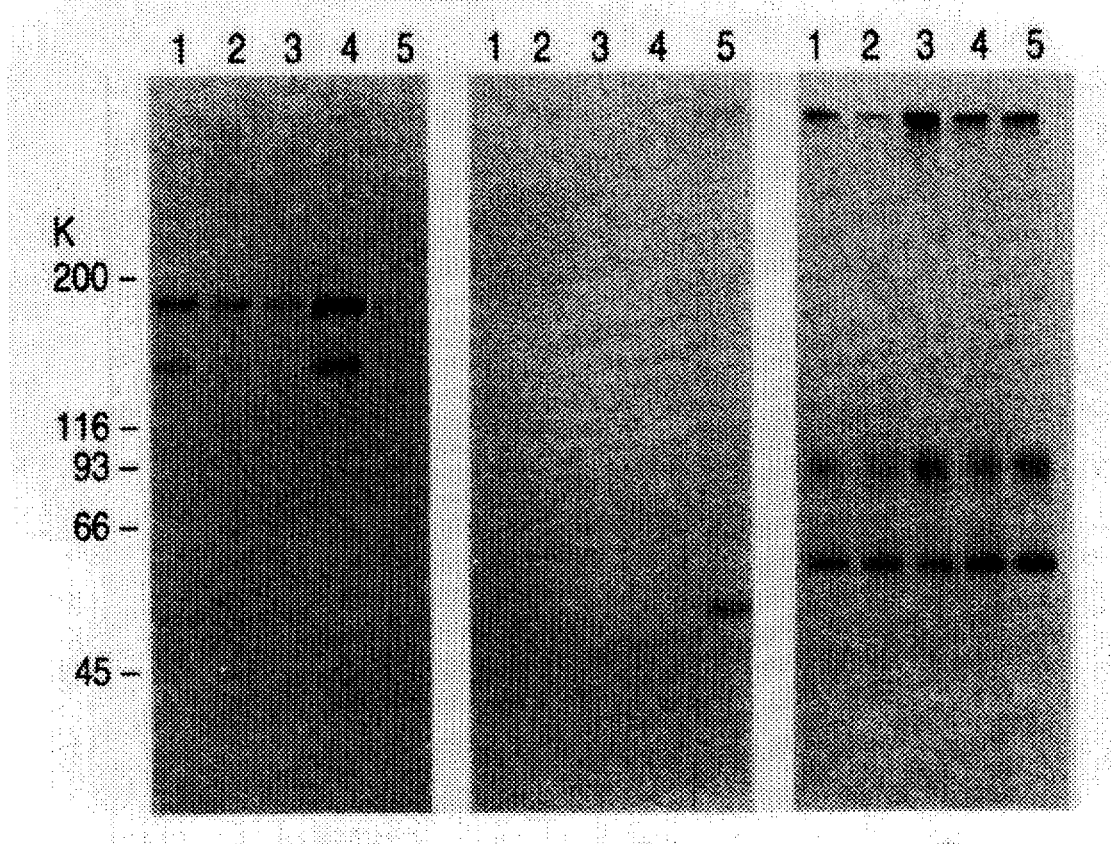
FIG. 10 is a photocopy of an autoradiogram showing specific reactivity of the neutralizing monoclonal antibodies with the recombinant S1 polypeptide. (A) vAcS-infected; (B) vAcS2-infected; (C) vAcS1-infected cell lysates. Immunoprecipitation with group A monoclonal antibodies, HE7-3 (lane 1), JB5-6 (lane 2), or HF8-8 (lane 3); with group B monoclonal antibody BB7-14 (Lane 4); or with anti-BCV polyclonal rabbit sera (lane 5).

Most of the critical epitopes for neutralization in transmissible gastroenteritis virus (TGE) (Jimenez et al., *J. Virol.* 60:131–139 (1986)), IBV (Cavanagh et al. *Virus Res.* 11:141–150 (1988)), and MHV (Talbot et al., *Virology* 132:250–260 (1984)) appear to be conformation-dependent. The S glycoprotein of BCV also contains at least two major conformation-dependent neutralizing epitopes, which are located on the S1 subunit as shown in FIG. 10. When we expressed a truncated form of the BCV S1 which extended to the middle (amino acids 1–516) of this S1 region, the polypeptide produced did not react with any of the monoclonal antibodies (unpublished observation). This observation implies that amino acids 456–593 of the BCV S1 subunit are associated with antigenic determinants for both groups of neutralizing antibodies.

Study of Membrane Fusion Mediated by the S2 Subunit of the Spike Protein

The following section was reported in *Virology* 180:395–399 (January 1991), the contents of which are specifically incorporated by reference. The hemagglutinin/esterase (HE), spike precursor (S) and the S1 and S2 subunits of the spike precursor protein of bovine coronavirus were expressed in *Spodoptera frugiperda* (Sf9) cells, and the cell-fusing activity of each recombinant glycoprotein was examined. Extensive syncytica formation was observed in cells infected with the S2 recombinant but not with the HE or S1 recombinant baculoviruses. Fusion of Sf9 cells expressing the intact S protein precursor was evident after trypsin treatment. These results demonstrate that proteolytic cleavage of the S spike precursor is required for fusion induction and that the fusion is mediated by the S2 subunit. The S2 subunit may play a role in fusion-penetration during bovine coronavirus infection. In order to identify the viral membrane glycoprotein which induces cell fusion by BCV, we expressed the HE, S and the S1 and S2 subunits of the S glycoprotein using recombinant baculoviruses, and examined the cell fusing activity of each recombinant polypeptide.

Briefly, in order to express the S1 subunit, the S gene was digested with Tth111I which cleaved the S gene within the sequences encoding the proteolytic cleavage site of the S precursor glycoprotein (nucleotides 2294–2295). The 5' 2294 nucleotide fragment was fused to a univeral translational terminator and inserted into the BamHI site of baculovirus transfer vector pAcYM1. Because the S2 subunit is derived by proteolytic cleavage of the S precursor polypeptide, the cDNA sequences encoding the S2 subunit lack a translation initiation codon and membrane translocation sequence. Therefore, the cDNA sequence encoding the S2 subunit was fused to the amino terminal signal sequence of the BCV HE glycoprotein. Plasmid pCVE3, which contains the cloned HE gene of BCV in the BamHI site of pTZ18R (Pharmacia), was digested with StyI, blunt-ended by S1 nuclease treatment and digested with SalI. A 2.0 kb ScaI-SalI fragment containing the cDNA sequences encoding the S2 subunit was obtained from the plasmid pCVE2, which contains the BCV S gene cloned in the BamHI site of pTZ18R, was ligated into the linearized pCVE3. This recombinant plasmid was subsequently modified by site directed mutagenesis yielding plasmid pAcDS2, which contained the complete BCV HE signal sequence fused to the S2 subunit through the alanine residue located at the amino terminus of the mature S2 subunit. The cloned genes were introduced into the genome of *Autographa californica* nuclear polyhedrosis virus (AcMNPV) by homologous recombination, and recombinant viruses were isolated by plaque hybridization and subsequent purification. Recombinant baculoviruses containing the HE, S, S1 and S2 genes were designated BVLHE, vAcS, vAcS1 and vAcS2, respectively.

Synthesis of BCV-specific polypeptides in *Spodoptera frugiperda* (Sf9) cells infected with the recombinant viruses was examined at 24 hr post-infection. Rabbit antisera to BCV precipitated a 57K polypeptide when analyzed under reducing conditions in the cells infected with BVLHE. The 57K polypeptide represents the monomer of the HE glycoprotein. Cells infected with vAcS produced a 170K polypeptide. This indicates that the S polypeptide was produced but proteolytic cleavage was not occurring to a significant extent in Sf9 cells. A 95K and an 80K polypeptide of the S1 and S2 subunits were immunoprecipitated from cells infected with vAcS1 and vAcS2, respectively.

In order to determine if any of the recombinant polypeptides were capable of inducing cell fusion, SF9 cells were infected with the recombinant baculoviruses at an moi of 5–10 p.f.u. per cell and incubated at 28° C. in TNM-FH media containing 10% fetal bovine serum. At 36 hr post-infection, the medium was replaced with TNM-FH in which the pH varied between 5.0–6.5. In order to examine syncytia formation at alkaline pH and because TNM-FH becomes turbid at alkaline pH, replicates of the infected cells were overlayed with 1.5% agarose in PBS which had been adjusted to a pH range of 5.0–8.0. Syncytia formation was monitored by phase contrast microscopy. Fusion was not detected in cultures infected with wild type AcMNPV, BVLHE or vAcS1 recombinant baculoviruses over the pH range examined. In contrast, fusion of vAcS-infected cells was apparent within 2 hr after a pH shift to 5.3. Extensive syncytica formation was observed in vAcS2-infected cells and continued to increase over 8 hr of observation until giant syncytia composed of approximately 100–200 cells were observed. When polyclonal BCV antibodies were included in the media, the fusion by the S and S2 polypeptides was partially inhibited. These observations demonstrate that the S2 subunit of the spike glycoprotein of BCV can induce cell fusion in the absence of other viral components.

The low level of fusion observed in vAcS-infected cells was thought to be due to a low level of cleavage of the S polypeptide. Partial cleavage of the recombinant S polypeptide of BCV in Sf9 cells has been demonstrated by pulse-chase experiment. In order to further determine the effect of proteolytic cleavage on the cell fusing activity of the recombinant S polypeptide precursor, vAcS-infected cells were treated with 20 μg/ml of trypsin for 10 min in PBS, pH 8.0 prior to a shift to pH 5.3. Trypsin treatment increased the extent of cell fusion in vAcS-infected cells to a level similar to that seen in vAcS2-infected cells. This result demonstrates that cleavage of the S precursor is required for induction of cell fusion. This also demonstrates that a polypeptide composed of signal sequence of the BCV HE glycoprotein followed by the S2 subunit of the BCV S glycoprotein induces cell-cell fusion in Sf9 cells.

The alanine residue at position 19 derived from the N-terminus of the S2 subunit provides a favorable context for cleavage of the HE signal sequence. The HE signal peptide of 18 amino acids does not seem to contribute to the fusogenicity of the recombinant S2 polypeptide since the HE polypeptide expressed with BVLHE did not induce fusion. Thus, the domain responsible for the cell fusion is located on the S2 subunit.

Fusion of insect cells infected with vAcS was dramatically increased by trypsin treatment. Therefore, it is clear that proteolytic cleavage is required to induce the fusion activity of both the recombinant S polypeptide in insect cells and the authentic S polypeptide produced in BCV-infected cells.

However, we have not detected fusion with the S1 subunit. A conformational change of the BCV S1 may expose the fusogenic domain of the S2 subunit by releasing the S1 rather than being directly involved in fusogenicity. Acidic conditions required for fusion in insect cells by the recombinant S2 subunit indicate the involvement of an acidic compartment in initiation of BCV infection.

As fusion of the viral envelope with cellular membranes is a critical requirement for virus infection, antisera directed against specific regions of the S2 subunit should identify the amino acids mediating membrane fusion and may determine if the fusogenic domain of the S2 polypeptide constitutes an important immunological determinant.

Deposit of Biological Materials

The following materials were deposited with the American Type Culture Collection (ATCC), 12301 Parklawn Drive, Rockville, Md. 20852, U.S.A. These deposits will be maintained under the terms of the Budapest Treaty on the deposit of microorganisms. The nucleotide sequences of the deposited materials are incorporated by reference herein, as well as the sequences of the polypeptides encoded thereby. In the event of any discrepancy between a sequence expressly disclosed herein and a deposited sequence, the deposited sequence is controlling. The deposit of such material, or its availability, is not the grant of a license to make, use, or sell any of the deposited materials.

| Material | ATCC Accession No. | Deposit Date |
|---|---|---|
| pT18E3 (E. coli JM105) | 68040 | 29 June 1989 |
| pT18E2 (E. coli JM105) | 68041 | 29 June 1989 |

While the present invention has been illustrated above by certain specific embodiments, the specific examples are not intended to limit the scope of the invention as described in the appended claims.

We claim:

1. A method of eliciting an immune response which reduces the severity of Bovine coronavirus (BCV) infection in a mammalian host, said method comprising:
   (a) providing a vaccine composition comprising a pharmaceutically acceptable carrier and at least one recombinant BCV polypeptide comprising a BCV neutralization epitope selected from the group consisting of E2 (S) having a molecular weight ranging from approximately 170 to 200 kDa, E3 (HE) having a molecular weight of approximately 120–140 kDa, a fragment of E2 and a fragment of E3; and
   (b) administering to the mammalian host an amount of the vaccine composition effective to elicit an immune response which reduces the severity of Bovine coronavirus infection.

2. The method of claim 1 wherein the vaccine composition further comprises an adjuvant.

3. The method of claim 1 wherein the polypeptide is E2 or a fragment of E2 comprising a neutralizing epitope.

4. The method of claim 3 wherein said vaccine composition further comprises a second recombinant BCV polypeptide comprising a BCV neutralization epitope comprising an E3 polypeptide or a fragment of E3.

5. The method of claim 1 wherein the polypeptide is E2.

6. The method of claim 5 wherein the vaccine composition further comprises a second recombinant BCV polypeptide comprising a BCV neutralization epitope comprising a BCV E3 polypeptide.

7. The method of claim 1 wherein the polypeptide is E3 or a fragment of E3 comprising a neutralization epitope.

8. The method of claim 1 wherein the polypeptide is E3.

9. A vaccine composition for reducing the severity of bovine coronavirus (BCV) infection in a mammalian host comprising a pharmaceutically acceptable carrier and an effective amount of at least one recombinant BCV polypeptide comprising a BCV neutralization epitope selected from the group consisting of E2 (S) having a molecular weight ranging from 170 to 200 kDa, E3 (HE) having a molecular weight of approximately 120–124 kDa, a fragment of E2 and a fragment of E3.

10. A composition comprising a pharmaceutically acceptable carrier and a recombinant BCV polypeptide comprising a BCV neutralization epitope selected from the group consisting of E2 (S) having a molecular weight ranging from 170–200 kDa, E3 (HE) having a molecular weight ranging from 120–124 kDa, a fragment of E2 and a fragment of E3.

11. The composition of claim 10 wherein the BCV polypeptide is full-length E2.

12. The composition of claim 10 wherein the BCV polypeptide is full-length E3.

13. The composition of claim 11 wherein the E2 polypeptide has the amino acid sequence shown in FIG. 3.

14. The composition of claim 12 wherein the E3 polypeptide has the amino acid sequence shown in FIG. 4.

15. The composition of claim 11 wherein the E2 polypeptide is glycosylated.

16. The composition of claim 12 wherein the E3 polypeptide is glycosylated.

17. The composition of claim 11 wherein the E2 polypeptide is not glycosylated.

18. The composition of claim 12 wherein the E3 polypeptide is not glycosylated.

* * * * *